(12) United States Patent
Wurster et al.

(10) Patent No.: US 6,593,324 B2
(45) Date of Patent: Jul. 15, 2003

(54) DERIVATIVES OF QUINOLINE AS ALPHA-2 ANTAGONISTS

(75) Inventors: Siegfried Wurster, Piikkiö (FI); Mia Engström, Turku (FI); Juha-Matti Savola, Turku (FI); Iisa Höglund, Turku (FI); Jukka Sallinen, Turku (FI); Antti Haapalinna, Turku (FI); Andrei Yurievitch Tauber, Helsinki (FI); Anna-Marja Katariina Hoffrén, Turku (FI); Harri Elias Salo, Turku (FI)

(73) Assignees: Orion Corporation, Espoo (FI); Oy Juvantia Pharma Ltd., Turku (FI)

( * ) Notice: Subject to any disclaimer, the term of this patent is extended or adjusted under 35 U.S.C. 154(b) by 0 days.

(21) Appl. No.: 09/794,277

(22) Filed: Feb. 28, 2001

(65) Prior Publication Data

US 2001/0046991 A1 Nov. 29, 2001

Related U.S. Application Data

(60) Provisional application No. 60/186,290, filed on Mar. 1, 2000.

(51) Int. Cl.$^7$ .................. C07D 215/00; C07D 401/12; C07D 411/00; A61K 31/495; A61K 31/147

(52) U.S. Cl. .................. 514/233.5; 514/233.07; 514/314; 544/363; 546/167

(58) Field of Search .................. 544/363; 514/253.06, 514/253.07, 314; 546/167

(56) References Cited

U.S. PATENT DOCUMENTS 6,288,082 B1 * 9/2001 Wissner et al. ............. 514/313

FOREIGN PATENT DOCUMENTS

| EP | 0 183 492 | 6/1986 |
|---|---|---|
| WO | WO 96/09294 | 3/1996 |
| WO | WO 99/28300 | 6/1999 |

OTHER PUBLICATIONS

Sathi et al., "New Quinolines as Potential CNS Agents," Arch. Pharm. 316, 767–772 (1983).
Radzikowski et al., "New Antitumor Compounds. Biological studies. IV. Antitumor properties of 21 new acridine derivatives," Acc. No. 1967: 401919 XP 002901810.
Kozyreva et al., "Synthesis and Study of the Anthelmintic Acttivity of Some N–Heterocycles Containing 4–(4'–Diethylcarbamoyl–1'–Piperazinyl) Phenylamine Substituents," Acc. No. 1972: 400153 XP 002901811.
Klopman et al., "Computer–Automated Structure Evaluation of Antileukemic 9–Anilinoacridines," Acc. No. 1987:628423 XP 002901812.
Mikailitsyn F.S. et al., Medicinskaja Parazitologija 1 parazitarnye bolezni, vol. 5, pp. 55–57 (1991).
Anti Haapalinna et al., "Evaluation of the effects of a specific $\alpha_2$–adrenoceptor antagonist, atipamozole, on $\alpha_1$– and $\alpha_2$–adrenoceptor subtype binding, brain neurochenistry and behaviour in comparison with yohimbine", Naunyn–Schmiedeberg's Arch Pharmacol, vol. 356, pp. 570–582 (1997).
Bruce Cain et al., "Potential Antitumor Agents. 23. 4'–(9–Acridinylamino)alkanesulfonanilide Congeners Bearing (Hydrophilic Functionality", Journal of Medicinal Chemistry, vol. 20, No. 8, pp. 987–996 (1977).
Adrienne Adams et al., "Interaction of DNA–Intercalating Antitumor Agents with Andrenoceptors", Molecular Pharmacology, vol. 27, pp. 480–491 (1985).
William Denny et al., "Pontetial Antitumor Agents. 36. Quantitative Relationships between Experimental Antitumor Activity, Toxicity, and Structure for the General Class of 9–Anilinoacridine Antitumor Agents", J. Med. Chem., vol. 25, pp. 276–315 (1982).
Anne Marjamäki et al., "Stable expression of recombinant human $\alpha_2$–adrenoceptor subtypes in two mammalian cell lines: characterization with [$^3$H]rauwolscine binding, inhibition of adenylate cyclase and RNase protection assay", Biochimica et Biophysica Acta, vol. 1134 pp. 169–177 (1992).
Jeffrey Jasper et al., "Ligand Efficacy and Potency at Recombinant $\alpha_2$ Adrenergic Receptors", Biochemical Pharmacology, vol. 55, pp. 1035–1043 (1998).

(List continued on next page.)

*Primary Examiner*—Richard L. Raymond
*Assistant Examiner*—Hong Liu
(74) *Attorney, Agent, or Firm*—Finnegan, Henderson, Farabow, Garrett & Dunner LLP (57) ABSTRACT

A compound of formula I,

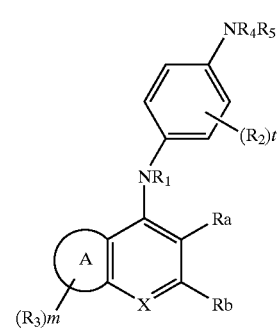

wherein A, Ra, Rb, $R_1$ to $R_5$, m and t are as defined as disclosed, or a pharmaceutically acceptable salt or ester thereof, useful as an alpha-2 antagonist. The compounds I can be used for the treatment of diseases or conditions where alpha-2 antagonists are indicated to be effective.

15 Claims, 1 Drawing Sheet

OTHER PUBLICATIONS

Katariina Pohjanoksa et al., "$\alpha_2$–Adrenoceptor regulation of adenylyl cyclase in CHO cells: dependence on receptor density, receptor subtype and current activity of adenylyl cyclase", Eur. Journal of Pharmacology, vol. 335, pp. 53–63 (1997).

Harry Scheinin et al., "Behavioural and neurochemical effects of antipamezole, a novel $\alpha_2$–adrenoceptor antagonist", Eur. Journal of Pharmacology, vol. 151, pp. 35–42 (1988).

Jukka Sallinen et al., "Genetic Alteration of $\alpha_{2c}$–Adrenoceptor Expression in Mice: Influence on Locomotor, Hypothermic, and Neurochemical Effects of Dexmedetomine, a Subtype–Nonselective $\alpha_2$–Adrenoceptor Agonist", Molecular Pharmacology, vol. 51 pp. 36–46 (1997).

Sallinen et al., "Genetic alteration of the $\alpha_2$–adrenoceptor subtype c in mice effects the development of behavioral despair and stress–induced increases in plasma corticosterone levels", Molecular Psychiatry, vol. 4, pp. 443–452 (1999).

Timo Kauppila et al., "Effects of atipamezole, a novel $\alpha_2$–adrenoceptor antagonist, in open–field, plus–maze, two compartment exploratory, and forced swimming tests in the rat", Eur. Journal of Pharmacology, vol. 205 pp. 117–182 (1991).

Steven Southwick et al., "Noradrenergic and Serotonergic Function in Posttraumatic Stress Disorder", Arch Gen. Psychiatry, vol. 54, pp. 749–758 (1997).

Crawley et al., "Baseline Exploratory Activity Predicts Anxiolytic Responsiveness to Diazepam in Five Mouse Strains", Brain Research Bulletin, vol. 8, pp. 609–612 (1982).

Sallinen et al., "D–Amphetamine and L–5–Hydroxytryptophan–Induced Behaviours in mice with Genetically–Altered expression of the $\alpha_{2c}$–Adrenergic Receptor Subtype", Neuroscience, vol. 86, No. 3, pp. 959–965 (1998).

Jukka Sallinen et al., "Adrenergic $\alpha_{2c}$–Receptors Modulate the Acoustic Startle Reflex, Prepulse Inhibition, and Aggression in Mice", The Journal of Neuroscience, vol. 18 (8), pp. 3035–3042 (1998).

Markus Björklund et al., "$\alpha_{2c}$–Adrenoceptor–Overexpressing Mice Are Impaired in Excuting Nonspatial Escape Strategies", Molecular Pharmacology, vol. 54, pp. 569–576 (1998).

* cited by examiner

DERIVATIVES OF QUINOLINE AS ALPHA-2 ANTAGONISTS

CROSS-REFERENCE TO RELATED APPLICATIONS

This application claims the benefit of priority under 35 U.S.C. § 119(e) to U.S. provisional application No. 60/186,290, filed on Mar. 1, 2000, the contents of which are incorporated by reference herein.

FIELD OF THE INVENTION

The present invention relates to therapeutically active derivatives of quinoline, including the pharmaceutically acceptable salts and esters thereof, and their use as alpha-2 antagonists.

BACKGROUND

Some compounds exhibiting alpha adrenergic activity are well known in the art. Those compounds may be used for the treatment of a wide variety of diseases and conditions of the peripheric system and the central nervous system (CNS).

The alpha adrenergic receptors are divided into alpha-1 and alpha-2 adrenoceptors, each of which are further divided into subtypes. Accordingly, alpha-2 adrenoceptors in humans have been subdivided into three pharmacological subtypes known as alpha-2A, alpha-2B and alpha-2C adrenoceptors. A fourth subtype, alpha-2D, is known in rat, bovine and porcine and it corresponds to alpha-2A in man. These subtypes have a distinct distribution in human and animal tissues. For instance, alpha-2C adrenoceptors are concentrated in the CNS, and they appear to play a role in the modulation of various CNS-mediated behavioural and physiological responses.

Compounds that are non-specific to any of the above-mentioned alpha-2 subtypes, and compounds that are specific to certain alpha-2 subtypes, are already known. For example, atipamezole is a non-specific alpha-2 antagonists. Atipamezole has been described in, for example, EP-A-183 492 (cf. p.13, compound XV) and A. Haapalinna et al., Naunyn-Schimiedeberg's Arch. Pharmacol. Vol. 356, 1997, p.570–582. U.S. Pat. No. 5,902,807 describes compounds that are selective antagonists for the alpha-2C subtype and may be used in the treatment of mental illnesses, e.g. mental disturbances induced by stress. Such compounds include, for example, MK-912 and BAM-1303. Furthermore, WO-A-99 28300 discloses substituted imidazole derivatives having agonist-like activity for alpha-2B or 2B/2C adrenoceptors. The disclosures of all documents cited above in this paragraph are incorporated by reference herein.

As to the derivatives of quinoline, Medicinskaja parazitologija I parazitarnye bolezni, vol.5, 1991, 55–7 (Mikhailitsyn F. S. et al.) and J. Med. Chem., vol.20(8), 1977, 987–996 (Cain F. C. et al.) describe, for example, acridine derivatives as anticancer and/or antiparasitic agents. In addition, a publication by Adams et al in 1985 (Mol. Pharm. 27, 480–491) reports on the binding of diquinolines, diacridines and a number of monoacridines on rat brain alpha-1-, alpha-2- and beta-adrenoceptors.

SUMMARY OF THE INVENTION

An object of the present invention is to provide further antagonists of alpha-2 adrenoceptors that can be used for the treatment of diseases or conditions of the pheripheric or central nervous system where alpha-2 antagonists are indicated to be useful. Accordingly, an object of the present invention is to provide further compounds to be used as alpha-2 antagonist agents in the treatment of mammals, including humans and animals.

Another object of the present invention is to provide further compounds useful as selective alpha-2C antagonist agents for the treatment of various disorders or conditions of the central nervous system where alpha-2C antagonists are indicated to be useful.

DETAILED DESCRIPTION OF THE INVENTION

One embodiment of the present invention covers a method of treatment using compounds of formula I:

wherein, $R_1$ is H or $(C_1-C_6)$alkyl;

each $R_2$ is independently OH, halogen, $(C_1-C_6)$alkyl, $(C_2-C_6)$alkenyl, $(C_1-C_6)$alkoxy, halo$(C_1-C_6)$alkyl, $NO_2$, $NH_2$, mono- or di$(C_1-C_6)$alkylamino, $(C_1-C_6)$alkyl-S— or hydroxy$(C_1-C_6)$alkyl;

A is a benzene ring or $(C_5-C_7)$cycloalkyl;

when A is a benzene ring each $R_3$ is independently OH, halogen, $(C_1-C_6)$alkyl, $(C_2-C_6)$alkenyl, $(C_1-C_6)$alkoxy, halo-$(C_1-C_6)$alkyl, $NO_2$, $NH_2$, mono- or di$(C_1-C_6)$alkylamino, $(C_1-C_6)$alkyl-CO—, mono- or di$(C_1-C_6)$-alkylcarbamoyl, $(C_1-C_6)$alkyl-S—, hydroxy$(C_1-C_6)$alkyl or $NH_2$—CO—;

when A is $(C_5-C_7)$cycloalkyl each $R_3$ is independently OH, halogen, $(C_1-C_6)$alkyl, $(C_1-C_6)$alkoxy, mono- or di$(C_1-C_6)$alkylamino or hydroxy$(C_1-C_6)$alkyl;

$R_4$ and $R_5$ form, together with the N-atom to which they are attached, wherein X is O or =$NR_6$; $R_6$ is H, OH, $NH_2$, $(C_1-C_6)$alkyl, $(C_2-C_6)$alkenyl, CN—$(C_1-C_6)$alkyl, $(C_1-C_6)$alkoxy-CO—$(C_1-C_6)$alkyl, $(C_1-C_6)$alkyl-CO—, $NH_2$—CO—, mono- or di$(C_1-C_6)$alkylcarbamoyl, hydroxy$(C_1-C_6)$alkyl, $(C_3-C_6)$cycloalkyl, phenyl, naphthyl or benzyl, wherein the said phenyl, naphthyl or benzyl is optionally substituted with one to three substituent(s) each independently being OH, halogen, $NO_2$, $NH_2$, $(C_1-C_6)$alkyl, $(C_1-C_6)$alkoxy, mono- or di$(C_1-C_6)$alkylamino or halo-$(C_1-C_6)$alkyl;

or $R_4$ and $R_5$ form, together with the N-atom to which they are attached, wherein n=1 or 2; $R_6$ is as defined above; and r=0 to 3;

or $R_4$ and $R_5$ form, together with the N-atom to which they are attached, 1-imidazolyl, 1-imidazolinyl or 1-triazolyl, each of which can optionally be substituted with one to three substituent(s) $R_7$ each independently being $(C_1-C_6)$alkyl or $NH_2$;

or one of $R_4$ and $R_5$ is —$SO_2R_8$ and the other of $R_4$ and $R_5$ is H or $(C_1-C_6)$alkyl; $R_8$ is $(C_1-C_6)$alkyl, phenyl, naphthyl or benzyl, wherein the said phenyl, naphthyl or benzyl is optionally substituted with one to three substituent(s) $R_9$ each independently being OH, halogen, $NO_2$, $NH_2$, $(C_1-C_6)$alkyl, $(C_1-C_6)$alkoxy or mono- or di$(C_1-C_6)$alkylamino;

Ra and Rb are independently H, OH, halogen, $(C_1-C_6)$alkyl, $(C_2-C_6)$alkenyl, $(C_2-C_6)$alkynyl, $(C_1-C_6)$alkoxy, halo$(C_1-C_6)$alkyl, $NO_2$, $NH_2$, mono- or di$(C_1-C_6)$alkylamino, $(C_1-C_6)$alkyl-S— or CN;

or Ra and Rb form, together with the carbon ring atoms to which they are attached, a condensed benzene ring optionally substituted with one to three substituent(s) $R'_3$ each independently being OH, halogen, $(C_1-C_6)$alkyl, $(C_2-C_6)$alkenyl, $(C_1-C_6)$alkoxy, halo-$(C_1-C_6)$alkyl, $NO_2$, $NH_2$, mono- or di$(C_1-C_6)$alkylamino, $(C_1-C_6)$alkyl-CO—, mono- or di$(C_1-C_6)$-alkylcarbamoyl or $(C_1-C_6)$alkyl-S—, hydroxy$(C_1-C_6)$alkyl or $NH_2$—CO—;

or Ra and Rb form, together with the carbon ring atoms to which they are attached, a condensed five to seven membered carbocyclic ring optionally substituted with one to four substituent(s) $R_{10}$ each independently being OH, halogen, $(C_1-C_6)$alkyl, $(C_1-C_6)$alkoxy, mono- or di$(C_1-C_6)$alkylamino or hydroxy$(C_1-C_6)$alkyl;

or Ra and Rb form, together with the carbon ring atoms to which they are attached, a condensed bicyclo[2.2.1]-heptane ring optionally substituted with one to four substituent(s) each independently being OH, halogen, $(C_1-C_6)$alkyl or $(C_1-C_6)$alkoxy;

or Ra and Rb form, together with the carbon ring atoms to which they are attached, a condensed five or six membered heterocyclic ring with one ring heteroatom =$NR_{11}$, which heterocyclic ring is optionally substituted with one to three substituent(s) $R_{10}$ as defined above; $R_{11}$ is H or $(C_1-C_6)$alkyl, or $R_{11}$ is phenyl optionally substituted with one to three substituents $R_{12}$ each independently being OH, halogen, $NO_2$, $NH_2$, $(C_1-C_6)$alkyl, $(C_1-C_6)$alkoxy or mono- or di$(C_1-C_6)$alkylamino;

m is 0 to 3; and t is 0 to 3, or pharmaceutically acceptable salts and esters thereof.

Those compounds can be used for the treatment of diseases or conditions where alpha-2 antagonists are indicated to be effective, and for the manufacture of a medicament for such treatment.

The following subgroups (1) to (18) of compounds of formula I taken alone or in any combination with each other are possible:

(1) A is a benzene ring;

(2) A is a $(C_5-C_7)$cycloalkyl;

(3) Ra and Rb are independently H, OH, halogen, $(C_1-C_6)$alkyl, $(C_2-C_6)$alkenyl, $(C_2-C_6)$alkynyl, $(C_1-C_6)$alkoxy, halo$(C_1-C_6)$alkyl, $NO_2$, $NH_2$, mono- or di$(C_1-C_6)$alkylamino, $(C_1-C_6)$alkyl-S— or CN; e.g. H, halogen, $(C_1-C_6)$alkyl, $(C_2-C_6)$alkenyl, $(C_2-C_6)$alkynyl, $(C_1-C_6)$alkoxy or halo$(C_1-C_6)$alkyl; such as H, halogen, $(C_1-C_6)$alkyl or $(C_1-C_6)$alkoxy; e.g. H or $(C_1-C_3)$alkyl, wherein the $(C_1-C_3)$alkyl includes both straight and branched chain radicals of up to 3 carbon atoms;

(4) Ra and Rb form, together with the carbon ring atoms to which they are attached, a condensed benzene ring unsubstituted or substituted with one to three, e.g. one or two, such as one, substituent(s) $R'_3$ each independently being OH, halogen, $(C_1-C_6)$alkyl, $(C_2-C_6)$alkenyl, $(C_1-C_6)$alkoxy, halo-$(C_1-C_6)$alkyl, $NO_2$, $NH_2$, mono- or di$(C_1-C_6)$alkylamino, $(C_1-C_6)$alkyl-CO—, $NH_2$—CO—, mono- or di$(C_1-C_6)$alkylcarbamoyl, $(C_1-C_6)$alkyl-S or hydroxy$(C_1-C_6)$alkyl; e.g. OH, halogen, $(C_1-C_6)$alkyl, $(C_2-C_6)$alkenyl or $(C_1-C_6)$alkoxy; such as halogen, $(C_1-C_6)$alkyl or $(C_1-C_6)$alkoxy; e.g. $(C_1-C_6)$alkyl or $(C_1-C_6)$alkoxy;

(5) Ra and Rb form, together with the carbon ring atoms to which they are attached, a condensed five to seven membered carbocyclic ring optionally substituted with one to four, e.g. one or two, such as one, substituent(s) $R_{10}$ each independently being OH, halogen, $(C_1-C_6)$alkyl or $(C_1-C_6)$alkoxy, mono- or di$(C_1-C_6)$alkylamino or hydroxy$(C_1-C_6)$alkyl; such as $(C_1-C_6)$alkyl or $(C_1-C_6)$alkoxy; e.g. $(C_1-C_6)$alkyl;

(6) Ra and Rb form, together with the carbon ring atoms to which they are attached, a condensed bicyclo[2.2.1]-heptane ring optionally substituted with one to four, e.g. one or two, such as one, substituent(s) each independently being OH, halogen, $(C_1-C_6)$alkyl or $(C_1-C_6)$alkoxy; e.g. $(C_1-C_6)$alkyl (7) Ra and Rb form, together with the carbon ring atoms to which they are attached, a condensed five or six membered heterocyclic ring with one ring heteroatom =$NR_{11}$, which heterocyclic ring is optionally substituted with one to three, e.g. one or two, such as one substituent(s) $R_{10}$ as defined above; and $R_{11}$ is H or $(C_1-C_6)$alkyl, or $R_{11}$ is phenyl optionally substituted with one to three, e.g. one or two, such as one, substituents $R_{12}$ each independently being OH, halogen, $NO_2$, $NH_2$, $(C_1-C_6)$alkyl or $(C_1-C_6)$alkoxy or mono- or di$(C_1-C_6)$alkylamino;

(8) $R_4$ and $R_5$ form, together with the N-atom, 1-piperazinyl which is 4-substituted with $R_6$, wherein $R_6$ is as defined above; e.g. $(C_1-C_6)$alkyl, $(C_2-C_6)$alkenyl, CN—$(C_1-C_6)$alkyl, $(C_1-C_6)$alkoxy-CO—$(C_1-C_6)$alkyl, $(C_1-C_6)$alkyl-CO—, $NH_2$—CO—, mono- or di$(C_1-C_6)$alkylcarbamoyl, hydroxy$(C_1-C_6)$alkyl, $(C_3-C_6)$cycloalkyl or optionally substituted benzyl; such as $(C_1-C_6)$alkyl, $(C_2-C_6)$alkenyl, hydroxy$(C_1-C_6)$alkyl, $(C_3-C_6)$cycloalkyl; e.g. $(C_1-C_6)$alkyl;

(9) $R_4$ and $R_5$ form, together with the N-atom, a morpholino ring;

(10) $R_4$ and $R_5$ form, together with the N-atom, a 1-piperidinyl or 1-pyrrolidinyl optionally substituted with $R_6$, wherein $R_6$ is as defined above, possibly $(C_1-C_6)$alkyl, $(C_2-C_6)$alkenyl, CN—$(C_1-C_6)$alkyl, $(C_1-C_6)$alkoxy-CO—$(C_1-C_6)$alkyl, $(C_1-C_6)$alkyl-CO—, $NH_2$—CO—, mono- or di$(C_1-C_6)$alkylcarbamoyl, hydroxy$(C_1-C_6)$alkyl or $(C_3-C_6)$cycloalkyl; such as $(C_1-C_6)$alkyl, $(C_2-C_6)$alkenyl, hydroxy$(C_1-C_6)$alkyl, $(C_3-C_6)$cycloalkyl; e.g. $(C_1-C_6)$alkyl;

(11) $R_4$ and $R_5$ form, together with the N-atom, 1-imidazolyl, 1-imidazolinyl or 1-triazolyl, each of which can optionally be substituted with one to three, e.g. one or two, such as one, substituent(s) $R_7$ each independently being $(C_1-C_6)$alkyl or $NH_2$; e.g. $R_4$ and $R_5$ form, together with the N-atom, 2-amino-imidazol-1-yl or 2-amino-imidazolin-1-yl;

(12) one of $R_4$ and $R_5$ is —$SO_2R_8$ and the other of $R_4$ and $R_5$ is H or $(C_1-C_6)$alkyl; $R_8$ is independently $(C_1-C_6)$alkyl, phenyl, naphthyl and benzyl, wherein the said phenyl, naphthyl or benzyl is optionally substituted with one to three, e.g. one or two, such as one, substituent(s) $R_9$ each independently being OH, halogen, $NO_2$, $NH_2$, $(C_1-C_6)$alkyl, $(C_1-C_6)$alkoxy or mono- or di$(C_1-C_6)$alkylamino;

(13) m is 0 to 3; e.g. 0, 1 or 2; e.g. 0 or 1; such as 0;

(14) t is 0 to 3; e.g. 0, 1 or 2; e.g. 0 or 1; such as 0;

(15) $R_1$ is H;

(16) $R_1$ is $(C_1-C_6)$alkyl;

(17) $R_2$ is independently OH, halogen, $(C_1-C_6)$alkyl, $(C_2-C_6)$alkenyl, $(C_1-C_6)$alkoxy, halo$(C_1-C_6)$alkyl, $NO_2$, $NH_2$, mono- or di$(C_1-C_6)$alkylamino, $(C_1-C_6)$alkyl-S— or hydroxy$(C_1-C_6)$alkyl; such as OH, halogen, $(C_1-C_6)$alkyl, $(C_1-C_6)$alkoxy or hydroxy$(C_1-C_6)$alkyl; e.g. $(C_1-C_6)$alkyl, $(C_1-C_6)$alkoxy; and/or (18) $R_3$ is independently OH, halogen, $(C_1-C_6)$alkyl, $(C_2-C_6)$alkenyl, $(C_1-C_6)$alkoxy, halo-$(C_1-C_6)$alkyl, $NO_2$, $NH_2$, mono- or di$(C_1-C_6)$alkylamino, $(C_1-C_6)$alkyl-CO—, mono- or di$(C_1-C_6)$-alkylcarbamoyl, $(C_1-C_6)$alkyl-S—, hydroxy$(C_1-C_6)$alkyl or $NH_2$—CO—; such as OH, halogen, $(C_1-C_6)$alkyl, $(C_2-C_6)$alkenyl, $(C_1-C_6)$alkoxy, halo-$(C_1-C_6)$alkyl; e.g. halogen, $(C_1-C_6)$alkyl or $(C_1-C_6)$alkoxy.

A possible subgroup of the compound of formula I is a compound of formula IA:

IA wherein $R_1$, $R_2$, $R_3$, $R_4$, $R_5$, $R_{10}$; m and t are as defined above; i is 1 to 3; and j is 0 to 4.

Another possible subgroup of the compound of formula I is a compound of formula IB:

IB wherein A, $R_1$, $R_2$, $R_3$, $R_4$, $R_5$, Ra, Rb, m and t are as defined above; and Ra and Rb are independently H, OH, halogen, $(C_1-C_6)$alkyl, $(C_2-C_6)$alkenyl, $(C_2-C_6)$alkynyl, $(C_1-C_6)$alkoxy, halo$(C_1-C_6)$alkyl, $NO_2$, $NH_2$, mono- or di$(C_1-C_6)$alkylamino, $(C_1-C_6)$alkyl-S— or CN; or Ra and Rb form, together with the carbon ring atoms to which they are attached, a condensed five to seven membered carbocyclic ring optionally substituted with one to three substituent(s) $R_{10}$; each independently being OH, halogen, $(C_1-C_6)$alkyl, $(C_1-C_6)$alkoxy, mono- or di$(C_1-C_6)$alkylamino or hydroxy$(C_1-C_6)$alkyl.

Another possible subgroup of the compound of formula I is a compound of formula IC:

IC wherein $R_1$, $R_2$, $R_3$, $R_4$, $R_5$, $R_{10}$, $R_{11}$, m and t are as defined above; i is 1 or 2; and j is 0 to 3.

Another possible subgroup of the compound of formula I is a compound of formula ID:

ID wherein $R_1$, $R_2$, $R_3$, $R'_3$, $R_4$, $R_5$, m and t are as defined above and p is 0 to 3; for example wherein m is 1 and $R_3$ is $(C_1-C_6)$alkoxy.

In a possible subgroup of the compound of formula I, IA, IB, IC or ID, $R_4$ and $R_5$ form, together with the N-atom to which they are attached, wherein X is =$NR_6$; $R_6$ is as defined above under formula I; such as $(C_1-C_6)$alkyl, $(C_2-C_6)$alkenyl, hydroxy $(C_1-C_6)$alkyl or $(C_3-C_6)$cycloalkyl; e.g. $(C_1-C_6)$alkyl.

Another possible subgroup of the compound of formula I is, wherein, when one of $R_4$ and $R_5$ is —$SO_2R_8$ and the other of $R_4$ and $R_5$ is H or $(C_1-C_6)$alkyl; then $R_8$ is not $(C_1-C_6)$alkyl.

Another possible subgroup of the compound of formula ID is, wherein, when one of $R_4$ and $R_5$ is —$SO_2R_8$ and the other of $R_4$ and $R_5$ is H or $(C_1-C_6)$alkyl; then $R_8$ is not $(C_1-C_6)$alkyl.

Another embodiment of the invention provides new compounds of formula II and a method of treatment using the compounds of formula II:

wherein,
$R_1$ is H or $(C_1-C_6)$alkyl;
each $R_2$ is independently OH, halogen, $(C_1-C_6)$alkyl, $(C_2-C_6)$alkenyl, $(C_1-C_6)$alkoxy, halo$(C_1-C_6)$alkyl, $NO_2$, $NH_2$, mono- or di$(C_1-C_6)$alkylamino, $(C_1-C_6)$alkyl-S— or hydroxy$(C_1-C_6)$alkyl;
A is a benzene ring or $(C_5-C_7)$cycloalkyl;
when A is a benzene ring each $R_3$ is independently OH, halogen, $(C_1-C_6)$alkyl, $(C_2-C_6)$alkenyl, $(C_1-C_6)$alkoxy, halo-$(C_1-C_6)$alkyl, $NO_2$, $NH_2$, mono- or di$(C_1-C_6)$alkylamino, $(C_1-C_6)$alkyl-CO—, mono- or di$(C_1-C_6)$-alkylcarbamoyl, $(C_1-C_6)$alkyl-S—, hydroxy$(C_1-C_6)$alkyl or $NH_2$—CO—;
when A is $(C_5-C_7)$cycloalkyl each $R_3$ is independently OH, halogen, $(C_1-C_6)$alkyl, $(C_1-C_6)$alkoxy, mono- or di$(C_1-C_6)$alkylamino or hydroxy$(C_1-C_6)$alkyl;
$R_4$ and $R_5$ form, together with the N-atom to which they are attached, wherein X is O or =$NR_6$; $R_6$ is H, OH, $NH_2$, $(C_1-C_6)$alkyl, $(C_2-C_6)$alkenyl, CN—$(C_1-C_6)$alkyl, $(C_1-C_6)$alkoxy-CO—$(C_1-C_6)$alkyl, $(C_1-C_6)$alkyl-CO—, $NH_2$—CO—, mono- or di$(C_1-C_6)$alkylcarbamoyl, hydroxy$(C_1-C_6)$alkyl, $(C_3-C_6)$cycloalkyl or benzyl, wherein the said benzyl is optionally substituted with one to three substituent(s) each independently being OH, halogen, $NO_2$, $NH_2$, $(C_1-C_6)$alkyl, $(C_1-C_6)$alkoxy, mono- or di$(C_1-C_6)$alkylamino or halo-$(C_1-C_6)$alkyl;

or $R_4$ and $R_5$ form, together with the N-atom to which they are attached, wherein n=1 or 2; $R_6$ is as defined above; and r=0 to 3;
or $R_4$ and $R_5$ form, together with the N-atom to which they are attached, 1-imidazolyl, 1-imidazolinyl or 1-triazolyl, each of which can optionally be substituted with one to three substituent(s) $R_7$ each independently being $(C_1-C_6)$alkyl or $NH_2$;
Ra and Rb are independently H, OH, halogen, $(C_1-C_6)$alkyl, $(C_2-C_6)$alkenyl, $(C_2-C_6)$alkynyl, $(C_1-C_6)$alkoxy, halo$(C_1-C_6)$alkyl, $NO_2$, $NH_2$, mono- or di$(C_1-C_6)$alkylamino, $(C_1-C_6)$alkyl-S— or CN;
or Ra and Rb form, together with the carbon ring atoms to which they are attached, a condensed benzene ring optionally substituted with one to three substituent(s) $R'_3$ each independently being OH, halogen, $(C_1-C_6)$alkyl, $(C_2-C_6)$alkenyl, $(C_1-C_6)$alkoxy, halo-$(C_1-C_6)$alkyl, $NO_2$, $NH_2$, mono- or di$(C_1-C_6)$alkylamino, $(C_1-C_6)$alkyl-CO—, mono- or di$(C_1-C_6)$-alkylcarbamoyl or $(C_1-C_6)$alkyl-S—, hydroxy$(C_1-C_6)$alkyl or $NH_2$—CO—;
or Ra and Rb form, together with the carbon ring atoms to which they are attached, a condensed five to seven membered carbocyclic ring optionally substituted with one to four substituent(s) $R_{10}$ each independently being OH, halogen, $(C_1-C_6)$alkyl, $(C_1-C_6)$alkoxy, mono- or di$(C_1-C_6)$alkylamino or hydroxy$(C_1-C_6)$alkyl;
or Ra and Rb form, together with the carbon ring atoms to which they are attached, a condensed bicyclo[2.2.1]-heptane ring optionally substituted with one to four substituent(s) each independently being OH, halogen, $(C_1-C_6)$alkyl or $(C_1-C_6)$alkoxy;
or Ra and Rb form, together with the carbon ring atoms to which they are attached, a condensed five or six membered heterocyclic ring with one ring heteroatom =$NR_{11}$, which heterocyclic ring is optionally substituted with one to three substituent(s) $R_{10}$ as defined above; $R_{11}$ is H or $(C_1-C_6)$alkyl, or RI 1 is phenyl optionally substituted with one to three substituents $R_{12}$ each independently being OH, halogen, $NO_2$, $NH_2$, $(C_1-C_6)$alkyl, $(C_1-C_6)$alkoxy or mono- or di$(C_1-C_6)$alkylamino;
m is 0 to 3; and
t is 0 to 3,
or of a pharmaceutically acceptable salt or ester thereof, with the provisos, that
a) when A is a benzene ring, m is 0 or 1, t is 0, $R_1$ is H, $R_3$ is Cl or $NO_2$, and Ra and Rb form, together with the carbon ring atoms to which they are attached, a condensed benzene ring, and X is $NR_6$, then $R_6$ is not H, —$CH_3$, —$CH_2CH_3$, —$COCH_3$, or —CO—$NH_2$;
b) when A is a benzene ring, then Ra and Rb are not at the same time H;
c) when A is a benzene ring, m is 1, t is 0, $R_1$ is H, and Ra and Rb form, together with the carbon ring atoms to which they are attached, a condensed benzene ring, which is optionally substituted with Br, and X is O, then $R_3$ is not $NO_2$ or —$OCH_3$;

d) when A is a benzene ring, m is 0, t is 0, $R_1$ is H, and Ra and Rb form, together with the carbon ring atoms to which they are attached, a condensed nonsubstituted benzene ring, then X is not 0;

e) the compound is not 4-[4-[(7-Chloro-2-methyl-4-quinolinyl)amino]phenyl]-1-diethylcarbamoylpiperazine, 4-[4-[(6-Chloro-2-methoxy-9-acridinyl)amino]phenyl]-1-diethylcarbamoylpiperazine, 6-amino-4-[[3-chloro-4-(1H-imidazol-1-yl)phenyl]amino]-7-metoxy-3-quinolinecarbonitrile or 4-[[3-chloro-4-(1H-imidazol-1-yl)phenyl]amino]-7-methoxy-6-nitro-3-quinolinecarbonitrile.

A possible subgroup of the compound of formula II is a compound of formula IIA,

IIA wherein $R_1$, $R_2$, $R_3$, $R_4$, $R_5$, $R_{10}$, m and t are as defined in formula II; i is 1 to 3; and j is 0 to 4; for example wherein i is 2, j is 0 or 1 and $R_{10}$ is $(C_1-C_3)$alkyl, wherein the $(C_1-C_3)$alkyl includes both straight and branched chain radicals of up to 3 carbon atoms; or wherein m is 0 or 1 and $R_3$ is $(C_1-C_3)$alkyl or halogen, wherein the $(C_1-C_3)$alkyl includes both straight and branched chain radicals of up to 3 carbon atoms; or wherein the compound is [4-(4-Methylpiperazin-1-yl)phenyl]-(1,2,3,4-tetrahydroacridin-9-yl)amine, 2-{4-[4-(1,2,3,4-Tetrahydroacridin-9-yl)aminophenyl]piperazin-1-yl}ethanol, [4-(4-Methylpiperazin-1-yl)phenyl]-(2-methyl-1,2,3,4-tetrahydro-acridin-9-yl)amine, (8-Fluoro-1,2,3,4-tetrahydroacridin-9-yl)-[4-(4-methylpiperazin-1-yl)phenyl]amine, [4-(4-Methylpiperazin-1-yl)phenyl]-(2,7-dimethyl-1,2,3,4-tetrahydroacridin-9-yl)amine, [4-(4-Methylpiperazin-1-yl)phenyl]-(7,8,9,10-tetrahydro-6H-cyclohepta[b]quinolin-11-yl)amine or [4-(4-Methylpiperazin-1-yl)phenyl]-(1,1,3,3-tetramethyl-1,2,3,4-tetrahydroacridin-9-yl)amine.

Another possible subgroup of the compound of formula II is a compound of formula IIB,

IIB wherein A, $R_1$, $R_2$, $R_3$, $R_4$, $R_5$, m and t are as defined in formula II; and Ra and Rb are independently H, OH, halogen, $(C_1-C_6)$alkyl, $(C_2-C_6)$alkenyl, $(C_2-C_6)$alkynyl, $(C_1-C_6)$alkoxy, halo$(C_1-C_6)$alkyl, $NO_2$, $NH_2$, mono- or di$(C_1-C_6)$alkylamino, $(C_1-C_6)$alkyl-S— or CN; or Ra and Rb form, together with the carbon ring atoms to which they are attached, a condensed five to seven membered carbocyclic ring optionally substituted with one to three substituent(s) $R_{10}$; each independently being OH, halogen, $(C_1-C_6)$alkyl, $(C_1-C_6)$alkoxy, mono- or di$(C_1-C_6)$alkylamino or hydroxy $(C_1-C_6)$alkyl; for example wherein A is a benzene ring; or wherein m is 0 or 1; or wherein $R_3$ is $(C_1-C_6)$alkyl or $(C_1-C_6)$alkoxy; or wherein Ra and Rb are independently H or $(C_1-C_3)$alkyl, wherein the $(C_1-C_3)$alkyl includes both straight and branched chain radicals of up to 3 carbon atoms; or wherein A is a six membered carbocyclic ring and Ra and Rb form, together with the carbon ring atoms to which they are attached, a condensed five to seven membered carbocyclic ring, wherein the carbocyclic ring can optionally be substituted with one to three substituent (s) each independently being OH, halogen, $(C_1-C_6)$alkyl, $(C_1-C_6)$alkoxy or hydroxy$(C_1-C_6)$alkyl; or wherein the compound is (3-Ethyl-2,8-dimethylquinolin-4-yl)-[4-(4-methylpiperizin-1-yl)phenyl]amine, (2-Methylquinolin-4-yl)-[4-(4-methylpiperazin-1-yl)phenyl]amine, (3-Ethyl-2,6-dimethylquinolin-4-yl)-[4-(4-methylpiperazin-1-yl)phenyl]amine, (3-Ethyl-6-methoxy-2-methylquinolin-4-yl)-[4-(4-methylpiperazin-1-yl)phenyl]amine, (3-Ethyl-2-methylquinolin-4-yl)-[4-(4-methylpiperazin-1-yl)phenyl]amine, 4-[4-(4-Methylpiperazin-1-yl)phenylamino]quinoline-3-carbonitrile, 3-Isopropyl-2-methylquinolin-4-yl)-[4-(4-methylpiperazin-1-yl)phenyl]amine, (2,3-Dimethylquinolin-4-yl)-[4-(4-methylpiperazin-1-yl)phenyl]amine, [4-(4-Methylpiperazin-1-yl)phenyl]-(1,2,3,4,5,6,7,8-octahydroacridin-9-yl)amine or (3-Ethyl-2-methylquinolin-4-yl)-methyl-[4-(4-methylpiperazin-1-yl)phenyl]amine.

Another possible subgroup of the compound of formula II is a compound of formula IIC,

IIC wherein $R_1$, $R_2$, $R_3$, $R_4$, $R_5$, $R_{10}$, $R_{11}$, m and t are as defined in formula II; i is 1 or 2; and j is 0 to 3.

Another possible subgroup of the compound of formula II is a compound of formula IID,

IID wherein $R_1$, $R_2$, $R_3$, $R'_3$, $R_4$, $R_5$, m and t are as defined in formula II; and p is 0 to 3; for example wherein m is 1 and $R_3$ is $(C_1-C_6)$alkoxy; or wherein the compound is 2-{4-[4-(Acridin-9-yl) aminophenyl]piperazin-1-yl}-ethanol, (4-Methoxyacridin-9-yl)-[4-(4-methylpiperazin-1-yl)-phenyl]amine, Acridin-9-yl-[4-(piperidin-1-yl)phenyl]amine, Acridin-9-yl-[4-(4-benzylpiperazin-1-yl)phenyl]amine, Acridin-9-yl-[4-(4-methylpiperidin-1-yl)phenyl]amine, Acridin-9-yl-[4-(3-hydroxymethylpiperidin-1-yl)-phenyl]amine, Acridin-9-yl-[4-pyrrolidin-1-yl)phenyl]amine, Acridin-9-yl-[4-(4-cyclopropylpiperazin-1-yl)phenyl]amine, Acridin-9-yl-[4-(4-isopropylpiperazine-1-yl)phenyl]amine, (Acridin-9-yl)-methyl-[4-(4-methylpiperazin-1-yl) phenyl]amine or Acridin-9-yl-[2,5-diethoxy-4-(morpholin-4-yl)phenyl]amine.

In a possible subgroup of the compound of Formula II, IIA, IIB, IIC, or IID, $R_4$ and $R_5$ form, together with the N-atom to which they are attached, wherein $R_6$ is $(C_1-C_6)$alkyl, $(C_1-C_6)$alkenyl, $(C_3-C_6)$ cycloalkyl or hydroxy$(C_1-C_6)$alkyl, for example, $R_6$ is $(C_1-C_6)$alkyl.

The compounds of formulae I and II and the subgroups IA, IB, IC, ID, IIA, IIB, IIC, and IID thereof, as well as the pharmaceutically acceptable esters and salts thereof, are referred to below as the compounds of the invention, unless otherwise indicated.

The compounds of the invention may have chiral carbon atom(s) in their structure. The invention includes within its scope all the possible stereoisomers of the compounds, including geometric isomers, e.g. Z and E isomers (cis and trans isomers), and optical isomers, e.g. diastereomers and enantiomers. Furthermore, the invention includes in its scope both the individual isomers and any mixtures thereof, e.g. racemic mixtures. The individual isomers may be obtained using the corresponding isomeric forms of the starting material or they may be separated after the preparation of the end compound according to conventional separation methods. For the separation of, for example, optical isomers, e.g. enantiomers, from the mixture thereof the conventional resolution methods, e.g. fractional crystallisation, may be used.

Physiologically acceptable salts, e.g. acid addition salts with both organic and inorganic acids are well known in the field of pharmaceuticals. Non-limiting examples of these salts include chlorides, bromides, sulfates, nitrates, phosphates, sulfonates, formates, tartrates, maleates, citrates, benzoates, salicylates and ascorbates. Pharmaceutically acceptable esters, when applicable, may be prepared by known methods using pharmaceutically acceptable acids that are conventional in the field of pharmaceuticals and that retain the pharmacological properties of the free form. Non-limiting examples of those esters include esters of aliphatic or aromatic alcohols, e.g. lower alkyl esters, e.g. methyl, ethyl and propyl esters.

Terms employed herein have the following meanings: A halogen or halo refers to fluorine, chlorine, bromine or iodine, e.g. fluorine or chlorine. The term $(C_1-C_6)$alkyl as employed herein as such or as part of another group includes both straight, and branched chain radicals of up to 6 carbon atoms, for example of 1 to 4 carbon atoms, e.g. methyl, ethyl, n-propyl, 1-propyl, n-butyl, 1-butyl or s-butyl. The term $(C_1-C_6)$alkoxy as such or as part of another group refers to —O—$(C_1-C_6)$alkyl, wherein $(C_1-C_6)$alkyl is as defined above. The term $(C_2-C_6)$alkenyl includes both straight and branched chain radicals of up to 6 carbon atoms, for example of 2 to 4 carbon atoms, containing (a) double bond(s). The term $(C_2-C_6)$alkynyl includes both straight and branched chain radicals of up to 6 carbon atoms, for example of 2 to 4 carbon atoms, containing (a) triple bond(s). The term halo-$(C_1-C_6)$alkyl refers to $(C_1-C_6)$alkyl radical, as defined above, that is substituted by one or more halo radicals as defined above, for example trifluoromethyl, difluoromethyl etc. The term mono- or di-$(C_1-C_6)$ alkylcarbamoyl refers to a carbamoyl radical which is N-substituted with one or two $(C_1-C_6)$alkyl radical(s), as defined above.

The compounds of the invention can be prepared analogously or according to a variety of synthetic routes known in the literature using suitable starting materials, for example, according to or analogous to methods described by B. F. Cain et al. in J. Med. Chem., vol.20(8), 1977, pp. 987–996, and by W. A. Denny et al. in J. Med. Chem., vol.25, 1982, p.276–315, the contents of which are hereby incorporated by reference.

In general, the compounds of the invention can be prepared e.g. analogously or according to the following reaction scheme 1:

Scheme 1 wherein Ra, Rb, $R_1$, $R_2$, $R_3$, $R_4$, $R_5$, m and t are as defined above.

The above reaction is a conventional acid-catalyzed coupling of the chloro-compound of formula III with a substi- tuted aromatic amine of formula IV. The reaction is carried out at room or elevated temperature in a suitable solvent, e.g. alcohol, such as methanol, in acidic conditions, to obtain the compound of formula I' which is then isolated from the reaction mixture in a usual manner.

The starting compounds III and IV are commercially available or can be prepared according to or analogously to the methods described in the literature (see e.g. J. Med. Chem., vol.20(8), 1977, pp. 987–996, and J. Med. Chem., vol.25, 1982, p.276–315, as mentioned above).

Accordingly, a substituted aromatic $NR_1$-amine IV can e.g. be prepared starting from the corresponding nitro compound which is reduced with a reducing agent, e.g. in the presence of $SnCl_2.H_2O$, in a suitable solvent, e.g. DMF, and optionally alkylated with $R_1$ in a manner known in the art, when $R_1=(C_{1-6})$alkyl is desired.

The starting material III can be prepared e.g. according to following scheme 2:

Scheme 2 wherein Ra, Rb, $R_3$, and m are as defined above.

In scheme 2 a compound V is reacted e.g. with thionyl chloride in the presence of a small amount of DMF, to obtain the 9-chlorinated reactant III. The reaction is carried out at room or elevated temperature.

It is obvious for a skilled person that, in the above reactions, any starting material or intermediate can be protected, if necessary, in a manner well known in the chemical field. Any protected functionality can subsequently be deprotected in a manner known in the art.

The above disclosed synthetic routes are meant to illustrate the preparation of the compounds of the invention, and the preparation is by no means limited thereto, i.e. other synthetic methods that are within the general knowledge of a skilled person are also possible.

The compounds of the invention may be converted, if desired, into their pharmaceutically acceptable salt or ester form using methods well known in the art.

The following examples are meant only for illustrating purposes and do not limit the scope of the invention defined in claims.

EXAMPLE 1

Acridin-9-yl-[4-(4-methylpiperazin-1 -yl)-phenyl]amine

Step 1

1.04 g (5.0 mmol) of N-(4-nitrophenyl)piperazine was dissolved in 5 ml of dimethylformamide. Sodium hydride (0.24 g, 6.0 mmol) was added to the reaction mixture in three portions under nitrogen atmosphere and cooling over a period of 10 min. After 30 min of stirring, 0.31 ml (6.0 mmol) of methyl iodide was added dropwise to the reaction mixture at 0° C. Stirring was continued for 1 h at room temperature, the reaction mixture was then evaporated to dryness, and purified by silica gel chromatography (methylene chloride:methanol:triethylamine 94:5:1) to yield 1.0 g (90%) of 1-methyl-4-(4-nitrophenyl)piperazine.

Step 2

0.999 g (4.5 mmol) of 1-methyl-4-(4-nitrophenyl)piperazine, 10.15 g (45 mmol) of tin(II)chloride dihydrate and 20 ml of dimethylformamide were mixed and stirred overnight at 80° C. Most of dimethylformamide was evaporated under vacuum. The remaining slurry was poured into ice water, neutralized with a sodium bicarbonate (sat.) solution, and filtered. The filtrate was extracted several times with ethylacetate and chloroform to provide 0.636 g (74%) of 4-(4-methylpiperazin-1-yl)aniline.

Step 3

0.488 g (2.5 mmol) of 9-(10H)acridone, 2.5 ml of thionyl chloride and a catalytic amount (a few drops) of dimethylformamide were mixed at 80° C. After 30 min of stirring, the reaction mixture was evaporated, the residue was dissolved in chloroform and poured into cold aqueous ammonia. The ammonia solution was extracted several times with chloroform. The combined organic phases were washed with 2M ammonia solution, dried over sodium sulfate and evaporated to obtain 0.517 g (97%) of 9-chloroacridine.

Step 4

0.191 g (1.0 mmol) of 4-(4-methylpiperazin-1-yl)aniline, 2.5 ml of methanol and a few drops of concentrated hydrochloric acid were mixed and heated under reflux. The 9-chloroacridine (1–1,5 equivalents) and 2.5 ml methanol were mixed separately and added to the reaction mixture in small portions. After 30 min of stirring, two drops of concentrated hydrochloric acid were added, and heating was continued for 2 h. The reaction mixture was then evaporated to dryness and purified by chromatography (silica gel column; gradient from 100% methylene chloride to 90% methylene chloride and 10% methanol; when 4-(4-methylpiperazin-1-yl)aniline eluted from the column, the eluent was changed to methylene chloride:methanol:triethylamine 94:5:1). A final amount of 0.126 g (34%, overall yield 12%) of the title compound in pure form was obtained.

$^1$H NMR (DMSO-$d_6$, 500 MHz): 8.05 (2H, m), 7.73 (2H, m), 7.66 (2H, m), 7.13 (2H, m), 6.97 (4H, m), 3.35 (4H, m), 2.98 (4H, m), 2.58 (3H, s); MS (EI$^+$): 368 (M$^+$)

EXAMPLE 2

Acridin-9-yl-[2,5-diethoxy-4-(morpholin-4-yl)phenyl]amine

Following the procedure outlined in Step 4 of Example 1, but substituting 2,5-diethoxy-4-morpholinoaniline dihydrochloride for 4-(4-methylpiperazin-1-yl)aniline, afforded the title compound with an overall yield of 23%

$^1$H NMR (CDCl$_3$, 500 MHz): 8.19 (2H, m), 8.13 (2H, m), 7.56 (1H, s), 7.42 (2H, m), 7.04 (2H, m), 6.42 (1H, s), 3.91 (4H, m), 3.15 (4H, m), 3,10 (4H, q, J=7.27 Hz), 1.41 (6H, t, J=7.27 Hz); MS (ESI$^+$ TOF): 444 (M$^+$)

EXAMPLE 3

Acridin-9-yl-[4-(morpholin-4-yl)phenyl]amine

Following the procedure outlined in Step 4 of Example 1, but substituting 4-(morpholin-1-yl)aniline for 4-(4-methylpiperazin-1-yl)aniline, afforded the title compound with an overall yield of 64%.

¹H NMR (CDCl₃, 500 MHz): 7.99 (4H, m), 7.55 (2H, m), 7.17 (2H, m), 7.04 (2H, m), 6.88 (2H, m), 3.88 (4H, m), 3.15 (4H, m); MS (ESI⁺ TOF): 356 (M⁺)

EXAMPLE 4

(3-Ethyl-2,8-dimethylquinolin-4-yl)-[4-(4-methylpiperazin-1-yl)phenyl]amine

Following the procedure outlined in Step 4 of Example 1, but substituting 4-chloro-2,8-dimethyl-3-ethylquinoline for 9-chloroacridine, afforded the title compound with 27% overall yield.

¹H NMR (CDCl₃, 500 MHz): 7.60 (1H, m), 7.41 (1H, m), 7.16 (1H, m), 6.79 (2H, m), 6.62 (2H, m), 5.62 (1H, s), 3.12 (4H, m), 2.79 (3H, s), 2.79(2H, q, J=7.63 Hz), 2.78 (3H, s), 2.59 (4H, m), 2.36 (3H, s), 1.15 (3H, t, J=7.63 Hz); MS (ESI⁺ TOF): 375 (M⁺)

EXAMPLE 5

(2-Methylquinolin-4-yl)-[4-(4-methylpiperazin-1-yl)phenyl]amine

Following the procedure outlined in Step 4 of Example 1, but substituting 4-chloro-2-methylquinoline for 9-chloroacridine, afforded the title compound with 24% overall yield.

¹H NMR (CDCl₃, 500 MHz): 8.02 (1H, m), 7.91 (1H, m), 7.64 (1, m), 7.44 (1H, m), 7.23 (2H, m), 7.00 (2H, m), 6.59(1H, m), 3.26 (4H, m), 2.61 (4H, m), 2.55 (3H, s), 2.38 (3H, s); MS (ESI⁺TOF): 333 (M⁺)

EXAMPLE 6

[4-(4-Methylpiperazin-1-yl)phenyl]-(quinolin-4-yl)amine

Following the procedure outlined in Step 4 of Example 1, but substituting 4-chloroquinoline for 9-chloroacridine, afforded the title compound with 11% overall yield.

¹H NMR (CDCl₃, 500 MHz): 8.28 (1H, m), 8.25 (1H, m), 8.06 (1H, m), 7.66 (1H, m), 7.50 (1H, m), 7.25 (2H, m), 6.97 (2H, m), 3.25 (4H, m), 2.64 (4H, m), 2.40 (3H, s); MS (ESI⁺ TOF): 319 (M⁺)

EXAMPLE 7

(3-Ethyl-2,6-dimethylquinolin-4-yl)-[4-(4-methylpiperazin-1-yl)phenyl]amine

Following the procedure outlined in Step 4 of Example 1, but substituting 4-chloro-1,6-dimethyl-3-ethylquinoline for 9-chloroacridine, afforded the title compound with 18% overall yield.

¹H NMR (CDCl₃, 500 MHz): 7.90 (1H, m), 7.49 (1H, m), 7.40 (1H, m), 6.81 (2H, m), 6.67 (2H, m), 3.12 (4H, m), 2.77 (2H, q, J=7.56 Hz), 2.78 (3H, s), 2.58 (4H, m), 2.36 (3H, s), 2.35 (3H, s), 1.15 (3H, t, J=7.56 Hz); MS (ESI⁺ TOF): 375 (M⁺)

EXAMPLE 8

(3-Ethyl-6-methoxy-2-methylquinolin-4-yl)-[4-(4-methylpiperazin-1 yl)phenyl]amine Following the procedure outlined in Step 4 of Example 1, but substituting 4-chloro-3-ethyl-6-methoxy-2-methylquinoline for 9-chloroacridine, afforded the title compound with 5% overall yield.

MS (ESI⁺ TOF): 391 (M⁺)

EXAMPLE 9

(3-Ethyl-2-methylquinolin-4-yl)-[4-(4-methylpiperazin-1-yl)phenyl]amine

Following the procedure outlined in Step 4 of Example 1, but substituting 4-chloro-3-ethyl-2-methylquinoline for 9-chloroacridine, afforded the title compound with 17% overall yield.

¹H NMR (CDCl₃, 500 MHz): 7.91 (1H, m), 7.72 (1H, m), 7.55 (1H, m), 7.25 (1H, m), 6.80 (2H, m), 6.67 (2H, m), 5.72 (1H, s), 3.11 (4H, m), 2.79 (2H, q, J=7.59 Hz), 2.77 (3H, s), 2.57 (4H, m), 2.34 (3H, s), 1.17 (3H, t, J=7.59 Hz); MS (ESI⁺ TOF): 361 (M⁺)

EXAMPLE 10

(4-Methoxyacridin-9-yl)-[4-(4-methylpiperazin-1-yl)phenyl]amine

Following the procedure outlined in Step 3 of Example 1, but substituting 9-hydroxy-4-methoxyacridine for 9-(10H)acridone, afforded 9-chloro-4-methoxyacridine, which was reacted with 4-(4-methylpiperazin-1-yl)aniline (according to the Step 4 in the procedure of Example 1) to obtain the title compound with 24% overall yield.

MS (ESI⁺ TOF): 399 (M⁺)

EXAMPLE 11

[4-(4-Methylpiperazin-1-yl)phenyl]-(1,2,3,4-tetrahydroacridin-9-yl)amine

Following the procedure outlined in Step 3 of Example 1, but substituting 1,2,3,4-tetrahydro-9-(10H)acridone for 9-(10H)acridone, afforded 9-chloro-1,2,3,4-tetrahydroacridine, which was reacted with 4-(4-methylpiperazin-1-yl)aniline (according to Step 4 in the procedure of Example 1) to obtain the title compound with 46% overall yield.

¹H NMR (CDCl₃, 500 MHz): 7.96 (1H, m), 7.72 (1H, m), 7.56 (1H, m), 7.27 (1H, m), 6.83 (2H, m), 6.73 (2H, m), 5.82 (1H, s), 3.14 (6H, m), 2.67 (2H, m), 2.58 (4H, m), 2.35 (3H, s), 1.94 (2H, m), 1.84 (2H, m); MS (ESI⁺ TOF): 373 (M⁺)

EXAMPLE 12

Acridin-9-yl-[4-(piperidin-1-yl)phenyl]amine 0.202 g (1.0 mmol) of 1-bromo-4-nitrobenzene and 0.20 ml of piperidine (2.0 mmol) were dissolved in 3 ml of dimethylsulfoxide. 0.207 g (1.5 mmol) of potassium carbonate was added and the reaction mixture was heated to 100° C. After 2 h 100 ml of water was added, and the mixture was extracted a few times with dichloromethane. The combined organic layers were dried over sodium sulfate and evaporated to obtain crude 4-(piperidin-1-yl)-1-nitrobenzene. Following the procedure outlined in Step 2 of Example 1, but substituting 4-piperidin-1-yl-1-nitrobenzene for 1-methyl-4-(4-nitrophenyl)piperazine, afforded 4-piperidin-1-ylaniline, which was reacted with 9-chloroacridine (according to Step 4 in the procedure of Example 1) to obtain the title compound with 6% overall yield.

¹H NMR (CDCl₃, 500 MHz): 8.05 (2H, m), 8.00 (2H, m), 7.48 (2H, m), 7.09 (4H, m), 6.86 (2H, m), 3.13 (4H, m), 1.71 (4H, m), 1.58 (2H, m); MS (ESI⁺ TOF): 354 (M⁺)

EXAMPLE 13

Acridin-9-yl-[4-(4-methylpiperidin-1-yl)phenyl]amine

Following the procedure of Example 12, but substituting 4-methylpiperidine for piperidine, afforded the title compound with 6% overall yield.

MS (ESI⁺ TOF): 368 (M⁺)

EXAMPLE 14

Acridin-9-yl-[4-(3-hydroxymethylpiperidin-1-yl)phenyl]amine

Following the procedure of Example 12, but substituting 3-hydroxymethylpiperidine for piperidine, afforded the title compound with 3% overall yield.

$^1$H NMR (CDCl$_3$, 500 MHz): 7.93 (2H, m), 7.81 (2H, m), 7.47 (2H, m), 7.04 (4H, m), 6.92 (2H, m), 3.68 (2H, m), 3.59 (2H, m), 2.78 (1H, m), 2.61 (1H, m), 1.95 (1H, br s), 1.83 (2H, m), 1.72 (1H, m), 1.23 (2H, m); MS (ESI$^+$ TOF): 384 (M$^+$)

EXAMPLE 15

Acridin-9-yl-[4-(pyrrolidin-1-yl)phenyl]amine

Following the procedure of Example 12, but substituting pyrrolidine for piperidine, afforded the title compound with 50% overall yield.

$^1$H NMR (CDCl$_3$, 500 MHz): 8.00 (4H, m), 7.56 (2H, m), 7.18 (2H, m), 7.00 (2H, m), 6.50 (2H, m), 3.27 (4H, m), 2.02 (4H, m); MS (ESI$^+$ TOF): 340 (M$^+$)

EXAMPLE 16

Acridin-9-yl-[4-(piperazine-1-yl)phenyl]amine

Following the procedure outlined in Step 2 of Example 1, but substituting N-(4-nitrophenyl)piperazine for 1-methyl-4-(4-nitrophenyl)piperazine, afforded 4-(piperazin-1-yl) aniline, which was reacted with 9-chloroacridine (according to Step 4 in the procedure of Example 1) to obtain the title compound with 16% overall yield.

$^1$H NMR (CD$_3$OD, 500 MHz): 8.21 (2H, m), 7.94 (4H, m), 7.42 (2H, m), 7.38 (2H, m), 7.20 (2H, m), 3.56 (4H, m), 3.43 (4H, m); MS (ESI$^+$ TOF): 355 (M$^+$)

EXAMPLE 17

Acridin-9-yl-[4-(4-acetylpiperazine-1-yl)phenyl]amine 35 mg (0.10 mmol) of 9-[4-(piperazin-1-yl)phenyl]aminoacridine (Example 16) was dissolved in 2 ml of chloroform, 7.1 μl (0.10 mmol) of acetyl chloride and catalytical amounts of pyridine and triethylamine were added. After 2 h of stirring at room temperature, the solvents were removed under vacuum, and the residue was purified by silica gel chromatography (eluent chloroform: methanol 6:1). The fractions with the title compound were combined, evaporated, taken up to water and extracted with chloroform. After drying over sodium sulfate, the organic layer was evaporated to obtain the title compound (6%, overall yield 1%).

MS (ESI$^+$ TOF): 397 (M$^+$)

EXAMPLE 18

Acridin-9-yl-[4-(4-benzylpiperazine-1-yl)phenyl]amine

Following the procedure outlined in Step 1 of Example 1, but substituting 9-[4-(piperazin-1-yl)phenyl]aminoacridine (Example 16) for N-(4-nitrophenyl)piperazine, and benzyl bromide for methyl iodide, afforded the title compound (15%, overall yield 2%)

$^1$H NMR (CDCl$_3$, 500 MHz): 8.00 (4H, m), 7.48 (2H, m), 7.34 (4H, m), 7.28 (1H, m), 7.12 (4H, m), 6.88 (2H, m), 3.59 (2H, s), 3.21 (4H, m), 2.63 (4H, m); MS (ESI$^+$ TOF): 445 (M$^+$)

EXAMPLE 19

Acridin-9-yl-[4-(4-isopropylpiperazine-1-yl)phenyl]amine

Following the procedure outlined in Step 1 of Example 1, but substituting 9-[4-(piperazin-1-yl)phenyl]aminoacridine (Example 16) for N-(4-nitrophenyl)piperazine, and isopropyl iodide for methyl iodide, afforded the title compound (11%, overall yield 2%).

MS (ESI$^+$ TOF): 397 (M$^+$)

EXAMPLE 20

2-{4-[4-(1,2,3,4-Tetrahydroacridin-9-yl)aminophenyl]piperazin-1-yl}ethanol 0.14 ml (2.0 mmol) of 2-bromoethanol and 0.17 ml (2.4 mmol) of acetyl chloride were dissolved in 2 ml of dichloromethane. 0.28 ml (2.0 mmol) of triethylamine was added, and the reaction mixture was stirred at room temperature. After 1 h 50 ml of dichloromethane was added to the reaction mixture, which was then washed with a sodium bicarbonate (sat.) solution, a 10% citric acid solution and water. The organic phase was dried over sodium sulfate and evaporated to obtain 0.241 g (72%) of 2-bromoethylacetate. Following the procedure outlined in Step 1 of Example 1, but substituting 2-bromoethylacetate for methyl iodide, afforded 2-[4-(4-nitrophenyl)piperazin-1-yl]ethylacetate (64%), which was reduced according to the procedure of Step 2 in Example 1 to give the corresponding amine 2-[4-(4-aminophenyl)piperazin-1-yl]ethylacetate in quantitative yield. 2-[4-(4-aminophenyl)piperazin-1-yl]ethylacetate was reacted with 9-chloro-1,2,3,4-tetrahydroacridine (according to the procedure of Step 4 in Example 1) to obtain 2-{4-[4-amino-(1,2,3,4-tetrahydroacridin-9-yl)phenyl]piperazin-1-yl}ethyl acetate with 47% yield. Treating the ester with 4 equivalents of lithium hydroxide in a dioxane/water solution overnight, afforded the title compound with 60% yield (overall yield 20%).

MS (ESI$^+$ TOF): 403 (M$^+$)

EXAMPLE 21

2-{4-[4-(Acridin-9-yl)aminophenyl]piperazin-1-yl}ethanol

Following the procedure outlined in Step 1 of Example 1, but substituting 9-[4-(piperazin-1-yl)phenyl]aminoacridine (Example 16) for N-(4-nitrophenyl)piperazine, and 2-bromoethyl-acetate for methyl iodide, afforded 2-{4-[4-amino-(1,2,3,4-tetrahydroacridin-9-yl)phenyl]piperazin-1-yl}ethyl acetate (31%). Treating the ester with 8 equivalents of lithium hydroxide in dioxane/water solution overnight, afforded the title compound with 37% yield (overall yield 2%).

MS (ESI$^+$ TOF): 399 (M$^+$)

EXAMPLE 22

Acridin-9-yl-[4-(4-cyclopropylpiperazine-1-yl)phenyl]amine 35 mg (0.10 mmol) of 9-[4-(piperazin-1-yl)phenyl]aminoacridine (Example 16) was dissolved in 1 ml of methanol. 57 μl (1.0 mmol) of acetic acid, 22 μl (0.11 mmol) of (1-ethoxycyclopropyloxy)-trimethylsilane and a small amount of 3 Å molecular sieves were added. The reaction mixture was stirred at room temperature under nitrogen atmosphere. After 30 min 28 mg (0.45 mmol) of sodium cyanoborohydride was added and the reaction mixture was heated at 50° C. over night. The solvents were removed under vacuum, and the residue was purified by chromatography (silica gel column, eluent chloroform/methanol 6:1) to obtain 3.8 mg (10%, overall yield 2%) of the title compound.

MS (ESI$^+$ TOF): 395 (M$^+$)

EXAMPLE 23

4-[4-(4-Methylpiperazin-1-yl)phenylamino]quinoline-3-carbonitrile 0.91 ml (10 mmol) of aniline and 1.69 g (10 mmol of ethyl(ethoxymethylene)cyanoacetate were dissolved in 10 ml of pyridine and heated under reflux. After 3 h pyridine was removed under vacuum, and the residue was purified by chromatography (silica gel column, eluent 1% methanol in dichloromethane). 1.08 g (50%) of ethyl(anilinomethylene)cyanoacetate were obtained. The compound was cyclized by heating in a biphenyl/phenyl ether mixture. After cooling a precipitate was filtered and washed with diethyl ether to give 4-hydroxyquinoline-3-carbonitrile (49%). Following the procedure outlined in Step 3 of Example 1, but substituting 4-hydroxyquinoline-3-carbonitrile for 9-(10H)acridone, 4-chloro-3-cyanoquinoline (90%) was obtained, which was reacted with 4-(4-methylpiperazin-1-yl)aniline (according to the procedure of Step 4 in Example 1), to afford the title compound with 12% yield (overall yield 3%).

$^1$H NMR (CDCl$_3$, 500 MHz): 8.66 (1H, s), 8.01 (1H, m), 7.78 (1H, m), 7.73 (1H, m), 7.42 (1H, m), 7.15 (2H, m), 6.94 (2H, m), 3.29 (4H, m), 2.63 (4H, m), 2.39 (3H, s); MS (ESI$^+$ TOF): 344 (M$^+$)

EXAMPLE 24

(3-Isopropyl-2-methylquinolin-4-yl)-[4-(4-methylpiperazin-1-yl)phenyl]amine 4.56 ml (50 mmol) of aniline and 10.7 ml (60 mmol) of ethyl 2-isopropylacetoacetate were mixed with 50 ml of chloroform. 0.48 g (2.5 mmol) of para-toluenesulfonic acid was added, and the reaction mixture was refluxed with continuous removal of the water produced in the reaction. After 2 d chloroform was removed in vacuum, and the residue was refluxed in 10 ml of phenyl ether. After cooling, the precipitate was filtered and washed with diethyl ether to give 4-hydroxy-3-isopropyl-2-methylquinoline (21%). Following the procedure of Step 3 in Example 1, but substituting 4-hydroxy-3-isopropyl-2-methylquinoline for 9-(10H) acridone, 4-chloro-3-isopropyl-2-methylquinoline (100%) was obtained, which was reacted with 4-(4-methylpiperazin-1-yl)aniline (following the procedure of Step 4 in Example 1), to afford the title compound with 61% yield (overall yield 13%).

$^1$H NMR (CDCl$_3$, 500 MHz): 7.95 (1H, m), 7.73 (1H, m), 7.54 (1H, m), 7.24 (1H, m), 6.79 (2H, m), 6.60 (2H, m), 5.72 (1H, s), 3.61 (1H, q, J=7.28), 3.11 (4H, m), 2.81 (3H, s), 2.57 (4H, m), 2.34 (3H, s), 1.38 (6H, d, J=7.28); MS (ESI$^+$ TOF): 375 (M$^+$)

EXAMPLE 25

(2,3-Dimethylquinolin-4-yl)-[4-(4-methylpiperazin-1-yl)phenyl]amine

Following the procedure of Example 24, but substituting ethyl 2-methylacetoacetate for ethyl 2-isopropylacetoacetate, afforded the title compound with 11% yield.

$^1$H NMR (CDCl$_3$, 500 MHz): 8.02 (1H, m), 7.78 (1H, m), 7.59 (1H, m), 7.33 (1H, m), 6.83 (2H, m), 6.69 (2H, m), 5.90 (1H, s), 3.13 (4H, m), 2.73 (3H, s), 2.58 (4H, m), 2.35 (3H, s), 2.24 (3H, s); MS (ESI$^+$ TOF): 347 (M$^+$)

EXAMPLE 26

[4-(4-Methylpiperazin-1-yl)phenyl]-(2-methyl-1,2,3,4-tetrahydro-acridin-9-yl)amine 1.37 g (10 mmol) of 2-aminobenzoic acid and 1.23 ml (10 mmol) of 4-methylcyclohexanone were dissolved in 10 ml of phosphorus oxychloride and the reaction mixture was heated under reflux in a nitrogen atmosphere. After 3 h most of the phosphorus oxychloride was removed under vacuum. The remaining brown syrup was poured into a cold sodium bicarbonate (sat.) solution and washed once with chloroform. The yellow precipitate forming in the basic water solution was filtered (2-methyl-1,2,3,4-tetrahydro-9-(10H)-acridone, 46%). Following the procedure of Step 3 in Example 1, but substituting 2-methyl-1,2,3,4-tetrahydro-9-(10H)acridone for 9-(10H)acridone, gave 9-chloro-2-methyl-1,2,3,4-tetrahydroacridine (40%), which was reacted with 4-(4-methylpiperazin-1-yl)aniline (according to the procedure of Step 4 in Example 1), to afford the title compound with 39% yield (overall yield 7%).

$^1$H NMR (CDCl$_3$, 500 MHz): 7.97 (1H, m), 7.70 (1H, m), 7.55 (1H, m), 7.24 (1H, m), 6.83 (2H, m), 6.72 (2H, m), 5.81 (1H, brs), 3.23 (1H, m), 3.14 (5H, m), 2.86 (1H, m), 2.57 (4H, m), 2.35 (3H, s), 2.24 (1H, m), 2.03 (1H, m), 1.93 (1H, m), 1.57 (1H, m), 1.10 (3H, d); MS (ESI$^+$ TOF): 387 (M$^+$)

EXAMPLE 27

[4-(4-methylpiperazin-1-yl)phenyl]-(7,8,9,10-tetrahydro-6H-cyclohepta[b]quinolin-11-yl)amine Following the procedure of Example 26, but substituting cycloheptanone for 4-methylcyclo-hexanone, afforded the title compound (0,2%)

(ESI$^+$ TOF): 387 (M$^+$)

EXAMPLE 28

[4-(4-Methylpiperazin-1-yl)phenyl]-(2,7-dimethyl-1,2,3,4-tetrahydroacridin-9-yl)amine Following the procedure of Example 26, but substituting 2-amino-5-methylbenzoic acid for 2-aminobenzoic acid, afforded the title compound (4%).

$^1$H NMR (CDCl$_3$, 500 MHz): 8.10 (1H, m), 7.43 (2H, m), 6.85 (2H, m), 6.83 (2H, m), 6.27 (1H, brs), 3.37 (1H, m), 3.18 (4H, m), 2.78 (1H, m), 2.61 (4H, m), 2.37 (3H, s), 2.33 (3H, s), 2.18 (1H, m), 2.02 (1H, m), 1.91 (1H, m), 1.52 (1H, m), 1.09 (1H, m), 1.10 (3H, d); MS (ESI$^+$ TOF): 401 (M$^+$)

EXAMPLE 29

(8-Fluoro-1,2,3,4-tetrahydroacridin-9-yl)-[4-(4-methylpiperazin-1-yl)phenyl]amine Following the procedure of Example 26, but substituting 2-amino-6-fluorobenzoic acid for 2-aminobenzoic acid, and cyclohexanone for 4-methylcyclohexanone, afforded the title compound (3%).

$^1$H NMR (CDCl$_3$, 500 MHz): 7.89 (1H, m), 7.51 (1H, m), 7.05 (1H, m), 6.87 (2H, m), 6.82 (2H, m), 3.22 (4H, m), 3.14 (2H, m), 2.66 (4H, m), 2.41 (3H, s), 2.34 (2H, m), 1.88 (2H, m), 1.67 (2H, m); MS (ESI$^+$ TOF): 391 (M$^+$)

EXAMPLE 30

[4-(4-Methylpiperazin-1-yl)phenyl]-(1,1,3,3-tetramethyl-1,2,3,4-tetrahydroacridin-9-yl)amine 1.49 ml (10 mmol) of ethyl 2-aminobenzoate and 1.73 ml (10 mmol) of 3,3,5,5-tetramethyl-cyclohexanone were mixed with 20 ml of toluene. 20 mg (0.1 mmol) of para-toluenesulfonic acid was added, and the reaction mixture was refluxed with continuous removal of the water produced in the reaction. After 9 h, toluene was removed under vacuum, and the residue was refluxed in 10 ml of phenyl ether. After cooling, the precipitate was filtered and washed with diethyl ether to obtain 1,1,3,3-tetramethyl-1,2,3,4-tetrahydro-9(10H)-acridone (18%). Following the procedure of Step 3 in Example 1, but substituting 1,1,3,3-tetramethyl-1,2,3,4-tetrahydro-9(10H)acridone for 9-(10H)acridone, gave 9-chloro-1,1,3,3-tetramethyl-1,2,3,4-tetrahydroacridine (21%), which was reacted with 4-(4-methylpiperazin-1-yl)aniline (according to the procedure of Step 4 in Example 1), to afford the title compound (3%, overall yield 0,1%).

MS (ESI$^+$ TOF): 429 (M$^+$)

EXAMPLE 31

(1,4-Methano-1,2,3,4-tetrahydroacridin-9-yl)-[4-(4-methylpiperazin-1-yl)phenyl]amine Following the procedure of Example 30, but substituting norcamphore for 3,3,5,5-tetramethyl-cyclohexanone, afforded the title compound (overall yield 1%).

$^1$H NMR (CDCl$_3$, 500 MHz): 7.99 (1H, m), 7.84 (1H, m), 7.58 (1H, m), 7.38 (1H, m), 7.02 (2H, m), 6.91 (2H, m), 6.13 (1H, s), 3.44 (1H, m), 3.21 (4H, m), 3.00 (1H, m), 2.61 (4H, m), 2.37 (3H, s), 1.97 (1H, m), 1.77 (2H, m), 1.48 (2H, m), 1.26 (1H, m); MS (ESI$^+$ TOF): 385 (M$^+$)

EXAMPLE 32

[4-(4-Methylpiperazin-1-yl)phenyl]-(1,2,3,4,5,6,7,8-octahydroacridin-9-yl)amine

Following the procedure of Example 30, but substituting ethyl 2-amino-1-cyclohexene-1-carboxylate for ethyl 2-aminobenzoate, and cyclohexanone for 3,3,5,5-tetramethylcyclo-hexanone, afforded the title compound (overall yield 0,2%).

MS (ESI$^+$ TOF): 377 (M$^+$)

EXAMPLE 33

(3-Ethyl-2-methylquinolin-4-yl)-methyl-[4-(4-methylpiperazin-1-yl)phenyl]amine

Following the procedure of Step 1 in Example 1, but substituting (3-ethyl-2-methylquinolin-4-yl)-[4-(4-methylpiperazin-1-yl)phenyl]amine (Example 9) for N-(4-nitrophenyl)piperazine, afforded the title compound (overall yield 12%).

$^1$H NMR (CDCl$_3$, 500 MHz): 8.03 (1H, m), 7.58 (2H, m), 7.34 (1H, m), 6.81 (2H, m), 6.42 (2H, m), 3.33 (3H, s), 3.07 (4H, m), 2.80 (3H, s), 2.71 (2H, q, J=7.50 Hz), 2.57 (4H, m), 2.34 (3H, s), 1.12 (3H, t, J=7.50 Hz); MS (ESI$^+$ TOF): 375 (M$^+$)

EXAMPLE 34

Acridin-9-yl-methyl-[4-(4-(methylpiperazin-1-yl)phenyl]amine

Following the procedure of Step 1 in Example 1, but substituting acridin-9-yl-[4-(4-methyl-piperazin-1-yl)-phenyl]-amine (Example 1) for N-(4-nitrophenyl)piperazine, afforded the title compound (overall yield 9%).

$^1$H NMR (CD$_3$OD, 500 MHz): 7.8 (2H, br s), 7.54 (2H, m), 7.48 (2H, m), 6.98 (4H, m), 6.79 (2H, m), 3.77 (3H, s), 3.18 (4H, m), 2.65 (4H, m), 2.36 (3H, s); MS (EI$^+$): 383 (M$^+$)

The compounds of the invention show interesting pharmacological properties, namely, they exhibit antagonistic affinity for alpha-2 adrenoceptors. This activity is demonstrated in the pharmacological tests presented below.

Experiment 1: Binding Affinity

The affinity of test compounds for the three human alpha-2-adrenoceptor subtypes (alpha-2A, alpha-2B and alpha-2C) was determined in binding competition assays with $^3$H-rauwolscine. The biological material consisted of membranes from Shionogi S115 cells stably transfected with one of the three human alpha-2 subtypes (A. Marjamäki et al., Biochem. Biophys. Acta, vol.1134, 1992, p.169). The membrane suspension (about 10 μg total protein per sample) and 1 nM of $^3$H-rauwolscine (specific activity 75–85 Ci/mmol) were incubated with a minimum of six concentrations of the test compound in a total volume of 90 μl (50 mM KH$_2$PO$_4$, pH 7.5, at room temperature). Non-specific binding was defined by 100 μM oxymetazoline and corresponded to 4–10% of the total binding. After 30 min at room temperature, the incubation was terminated by rapid filtration (TomTec 96 harvester) through presoaked GF/B glass-fiber mats (Wallac Oy) and three washes with ice-cold 50 mM KH$_2$PO$_4$ (pH 7.5, at room temperature). After drying, a solid scintillate (Meltilex; Wallac Oy) was melted on filter mats, and the radioactivity was measured (BetaPlate; Wallac Oy). The analysis of the experiments was carried out by non-linear least square curve fitting. IC$_{50}$'s were converted to Ki's by using the equation of Cheng-Prussoff ($K_i$=IC$_{50}$/(1+[$^3$H-ligand]/K$_{d, \ ^3H-ligand}$)) The K$_i$ values for Compound 1 obtained in a minimum of three independent experiments were:

alpha-2A Adrenoceptor: 3150±50 nM
alpha-2B Adrenoceptor: 1470±130 nM
alpha-2C Adrenoceptor: 28±2 nM Experiment II: Antagonist Activity Antagonist activity was determined as the ability of compounds to competetively inhibit epinephrine-stimulated $^{35}$S-GTPγS binding to G proteins (J. R. Jasper et al., Biochem. Pharmacol., vol.55, 1998, p.1035) in membranes of CHO cells stably transfected with one of the three human alpha-2 subtypes (K. Pohjanoksa et al., Eur. J. Pharmacol., vol.335, 1997, p.53). Membranes (5–10 μg of protein per sample) and 12 concentrations of test compound were preincubated for 30 min at room temperature in 50 mM Tris, 5 mM MgCl$_2$, 150 mM NaCl, 1 mM DTT, 1 mM EDTA, 10 μM GDP, 30 μM ascorbic acid, pH 7.4, with a fixed concentration of epinephrine (5 μM for alpha-2A, 15 μM for alpha-2B, 5 μM for alpha-2C). Then trace amounts of $^{35}$S-GTPγS (0.08 nM-0.15 nM, specific activity 1250 Ci/mmol) were added to the incubation mixture. After an additional 30 min at room temperature, the incubation was terminated by rapid vacuum filtration through glass fiber filter. Filters were washed three times with 5 ml ice cold wash buffer (20 mM Tris, 5 mM MgCl$_2$, 1 mM EDTA, pH 7.4, at room temperature), dried and counted for radioactivity in a scintillation counter. Analysis of experiments was carried out by nonlinear least square fitting. Experiments were repeated at least three times. The K$_B$ values of Compound 1 were found to correspond to:

alpha-2A Adrenoceptor: 1495±270 nM
alpha-2B Adrenoceptor: 2175±345 nM
alpha-2C Adrenoceptor: 16±6 nM Experiment III: Antagonism of Dexmedetomidine-induced Locomotor Inhibition by Atipamezole but not by Compound 1; Demonstration of in vivo Alpha2C Selectivity of Compound 1

Dexmedetomidine and atipamezole are very potent and specific alpha-2 adrenoceptor agonists and antagonists, respectively, which lack alpha-2 subtype selectivity (H. Scheinin et al., European Journal of Pharmacology, Molecular Section, vol.151(1), 1988, p.35–42). The alpha-2 agonist-induced sedation is known to be an alpha-2A-mediated phenomenon that can be antagonised by alpha-2 antagonists (J. Sallinen et al., Mol. Pharmacol. Vol.51, 1997, p.36–46, and A. Haapalinna et al., Naunyn-Schimiedeberg's Arch. Pharmacol. Vol.356, 1997, p.570–582). The sedative effect of alpha-2 agonists in mice is measured by the inhibition on locomotor activity. Therefore, we compared the ability of Compound I and atipamezole to antagonise the dexmedetomidine-induced locomotor inhibition to evaluate the in vivo alpha-2A adrenoceptor antagonism (and alpha-2C selectivity) of these compounds.

Spontaneous locomotor activity of a total of 76 male NMRI mice (B&K, Sweden) was measured by placing individual animals into a polypropylene animal cage (38× 22×15 cm). The cages were surrounded with an infrared photobeam frame system designed for activity measurements (Photobeam Activity System PAS, Cage Rack, San Diego Instruments, San Diego, Calif., USA). The animals were injected with various doses of either Compound 1 or atipamezole 20 min before injection of dexmedetomidine (50 nmol/kg s.c.). Spontaneous locomotor activity was measured 20 min after dexmedetomidine injection.

Figure 1:
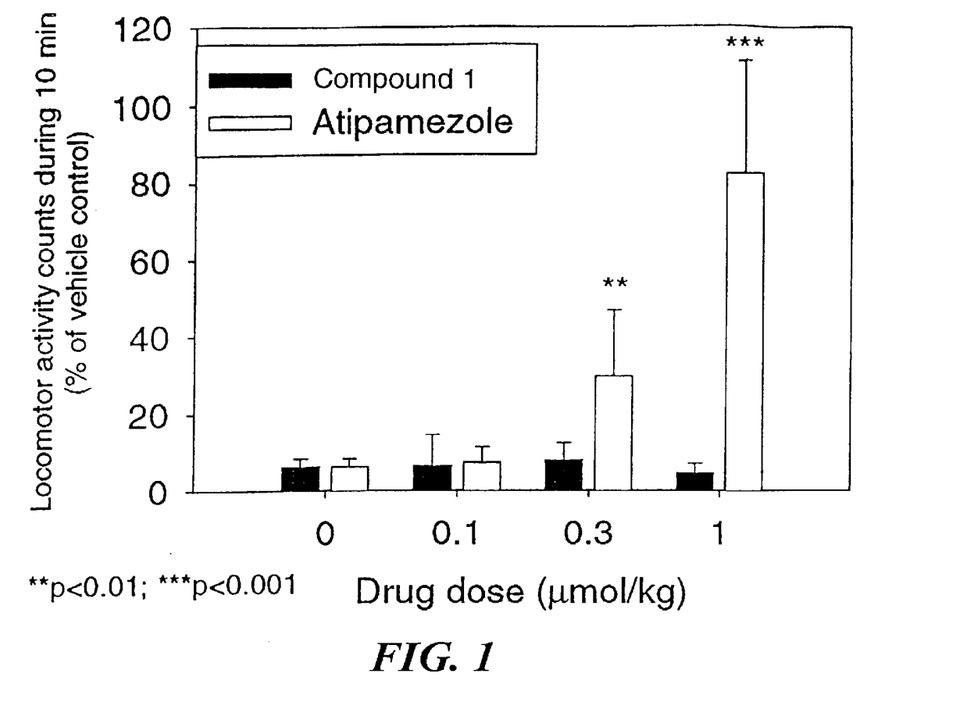
FIG. 1 shows the effects of atipamezole and compound 1 on dexmedetomidine-induced hypolocomotion.

The results presented in FIG. 1 show that atipamezole inhibited dexmedetomidine-induced sedation with doses 0.3 and 1.0 $\mu$mol/kg s.c. (p<0.01) as was expected. In contrast, Compound 1 did not antagonise the alpha-2-agonist-induced sedation at all, demonstrating the lack of alpha-2A antagonism and the alpha-2C selectivity of Compound 1 in vivo.

Experiment IV:

Stress-protective Effect of Compound 1 in the Mouse Forced Swimming Test

Exposure of a test animal to an intense stressful stimulus has been observed to propagate a state of behavioural despair. This can be observed for example employing the forced swimming test, in which a rat or mouse is put into a water-filled cylinder. After a vigorous period of attempts to escape animals adopt an immobile floating posture; the extent of the immobile period is monitored and can be reduced by antidepressants and stress-protective agents. Transgenic mice that lack functional alpha-2C adrenoceptor tolerated swim-stress better than their similarly treated wild-type controls (J. Sallinen et al., Mol. Psychiatry, vol.4, 1999, p.443–452). Therefore, an increase in the forced swimming activity can be used as a measure of in vivo alpha-2C selective antagonism of a compound. The non-selective antagonist atipamezole did not have a clear stress-protective effect and even increased vocalizations of test animals (T. Kauppila et al., Eur. J. Pharmacol., vol.205, 1991, p.177–182). This may have resulted from the simultaneous alpha-2A antagonistic activity of atipamezole, since conventionally non-selective alpha-2 adrenoceptor antagonists, such as yohimbine, have been found to be anxiogenic (S. Southwick et al., Arch. Gen. Psychiatry, vol.54, 1997, p.749–758).

Figure 2:
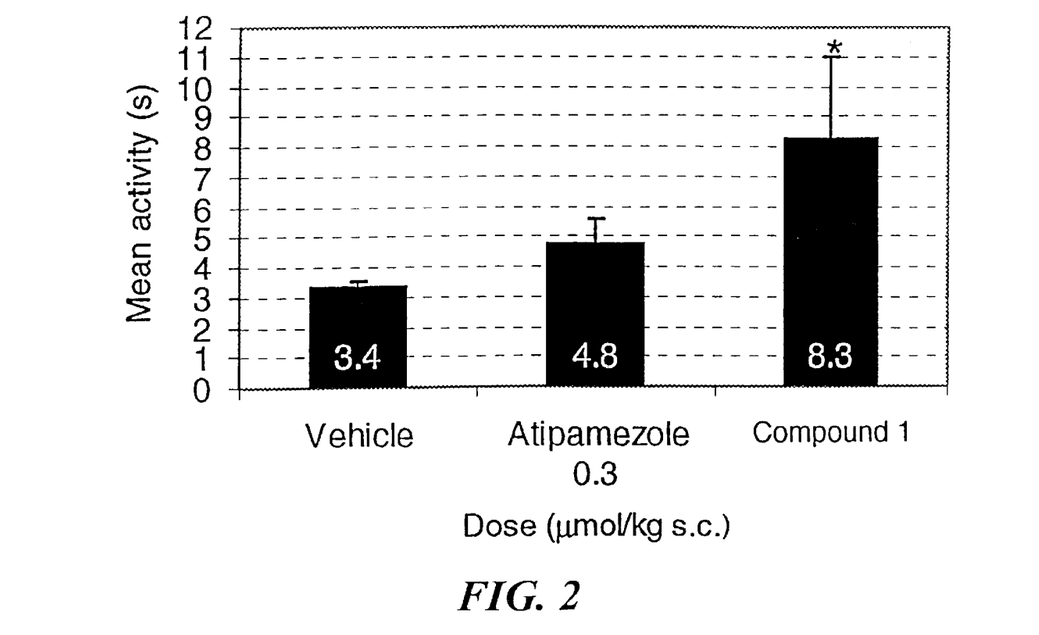
FIG. 2 shows the effects of atipamezole and compound 1 in a forced swimming test in Balb/c mice.

The forced swim test was conducted as originally described employing the stress sensitive (J. Crawley and L. Davis, Brain Research Bulletin, vol.8, 1982, p.609–612, and U.S. Pat. No. 5,902,807) Balb/c mouse strain (B&K, Sweden). The mice were administered either with vehicle (0.1% DMSO, 5 ml/kg subcutaneously), Compound 10.3 $\mu$mol/kg, or atipamezole 0.3 $\mu$mol/kg 40 min before putting the mice into a vessel (10 cm diameter, 18.5 cm height, filled with 25° C. water up to 8 cm height). The cumulative activity of each mouse was measured between 2 and 6 min after introduction to the vessel. Only vigorous attempts to escape (climbing) were registered. The mice (a total of 96) were tested only once. The results are shown in FIG. 2.

Mice administered with Compound 1 tolerated clearly better stress-induced propagation of behavioural despair when compared to vehicle injected group of mice (1-way ANOVA, followed by LSD post hoc test; p=0.013) as was expected for an alpha-2C selective compound. Atipamezole did not have any clear effect on the activity compared to control mice (p=0.52). A possible marginal effect of atipamezole was expected, since this subtype-non-selective alpha-2 antagonist blocks also the alpha-2C adrenoceptors. On the other hand the employed 0.3 $\mu$mol/kg dose of atipamezole was shown to have also alpha2A antagonism in vivo (FIG. 1). The employed doses of atipamezole have also been shown to have clear neurochemical effects, i.e. to stimulate noradrenaline release in brain (A. Haapalinna et al., Naunyn-Schimiedeberg's Arch. Pharmacol. Vol.356, 1997, p.570–582). Therefore, the results support that alpha-2A adrenoceptor antagonism of atipamezole can counteract the stress-protective and antidepressant effects of alpha-2C antagonism in vivo (J. Sallinen et al., Mol. Psychiatry, vol.4, 1999, p.443–452, and U.S. Pat. No. 5,902,807).

In general, the compounds of the invention exhibiting alpha-2 adrenoceptor antagonistic activity may be useful for the treatment of diseases or conditions wherein alpha-2 antagonists are effective. For example, the compounds can be used to treat disorders of the central nervous system, male sexual impotence, orthostatic hypotension, non-insulin dependent diabetes, and obesity, for example, disorders of the central nervous system. The compounds can also be used to reverse effects induced by alpha-2 agonists. Disorders of the central nervous system treatable with the compounds of the invention include depression, anxiety, post-traumatic stress disorder, schizophrenia, Parkinson's disease, and other movement disorders.

The selective alpha-2C antagonists of the present invention may be used for the treatment of various diseases or conditions of CNS-system where alpha2C-antagonists are indicated to be beneficial (see e.g. U.S. Pat. No. 5,902,807, J. Sallinen et al., Neuroscience, vol. 86, 1998, p.959–965, J. Sallinen et al., J. Neuroscience, vol. 18, 1998, p.3035–3042, and M. Bjorklund et al., Molecular Pharmacology, vol.54, 1998, p.569–76, the contents of which are hereby incorporated by reference), for example, in the treatment of schizophrenia and depression. Furthermore, the present alpha-antagonists can be used as stress-protective agents, or as agents for the treatment of CNS-disorders induced by stress, e.g. of post-traumatic stress disorder, as indicated, for example, in U.S. Pat. No. 5,902,807 cited above. Because alpha-2C antagonists appear to stimulate central dopaminergic activity, they can be used as antiparkinsonian agents in Parkinson's disease and other movement disorders. Moreover, the present alpha-2C antagonists may also exhibit cognition enhancing properties and thus may be used in the treatment of Alzheimer's disease and other dementias.

Due to the selectivity of tissue distribution, the alpha-2C antagonists of the invention have less or no undesirable side-effects, such as cardiovascular effects.

The compounds of the invention may be administered enterally, topically or parenterally.

The compounds of the invention may be formulated alone or together with another active ingredient and/or together with a pharmaceutically acceptable diluent, carrier and/or excipient in different pharmaceutical unit dosage forms, e.g. tablets, capsules, solutions, emulsions and powders etc., depending on the route of administration, using conventional techniques. The pharmaceutically acceptable diluent, carrier and/or excipient can be selected from those conventionally used in the field of pharmaceuticals noticing the chosen route of administration.

The amount of the active ingredient in a dosage form may vary from, for example, 0.01 to 75 weight-% depending on, for example, the type of the dosage form.

The specific dose level of the compounds of the invention depends on several factors such as the compound to be administered, the species, age and the sex of the subject to be treated, the condition to be treated and on the route and method of administration. Accordingly, the dosage for parenteral administration is typically from 0.5 μg/kg to 10 mg/kg per day and that for oral administration is from 5 μg/kg to 100 mg/kg for an adult male.

The present invention further provides a compound of the invention for use as alpha-2 antagonist. Furthermore, a method for the treatment of diseases or conditions where alpha-2 antagonists, e.g. alpha-2C antagonists, are indicated to be useful, e.g. a method for the treatment of diseases or conditions of the central nervous system, is provided. In such a method a therapeutically effective amount of a compound of the invention is administered to a subject in need of such treatment. The use of the compounds of the invention for the manufacture of a medicament to be used for the above indications is also provided.

Those skilled in the art will appreciate that the embodiments described in this application could be modified without departing from the broad inventive concept. Those skilled in the art also understand that the invention is not limited to the particular disclosed embodiments, but is intended to also cover modifications to the embodiments that are within the spirit and scope of the invention.

We claim:

1. A compound of formula II,

II or a pharmaceutically acceptable salt or ester thereof, wherein, $R_1$ is H or $(C_1–C_6)$alkyl;

each $R_2$ is independently OH, halogen, $(C_1–C_6)$alkyl, $(C_2–C_6)$alkenyl, $(C_1–C_6)$alkoxy, halo$(C_1–C_6)$alkyl, $NO_2$, $NH_2$, mono- or di$(C_1–C_6)$alkylamino, $(C_1–C_6)$alkyl-S- or hydroxy$(C_1–C_6)$alkyl;

A is a benzene ring or $(C_5–C_7)$cycloalkyl;

when A is a benzene ring each $R_3$ is independently OH, halogen, $(C_1–C_6)$alkyl, $(C_2–C_6)$alkenyl, $(C_1–C_6)$alkoxy, halo-$(C_1–C_6)$alkyl, $NO_2$, $NH_2$, mono- or di$(C_1–C_6)$alkylamino, $(C_1–C_6)$alkyl-CO-, mono- or di$(C_1–C_6)$-alkylcarbamoyl, $(C_1–C_6)$alkyl-S-, hydroxy $(C_1–C_6)$alkyl or $NH_2$—CO—;

when A is $(C_5–C_7)$cycloalkyl each $R_3$ is independently OH, halogen, $(C_1–C_6)$alkyl, $(C_1–C_6)$alkoxy, mono- or di$(C_1–C_6)$alkylamino or hydroxy$(C_1–C_6)$alkyl;

$R_4$ and $R_5$ form, together with the N-atom to which they are attached, wherein X is O or $=NR_6$; $R_6$ is H, OH, $NH_2$, $(C_1–C_6)$alkyl, $(C_2–C_6)$alkenyl, CN-$(C_1–C_6)$alkyl, $(C_1–C_6)$alkoxy-CO-$(C_1–C_6)$alkyl, $(C_1–C_6)$alkyl-CO-, $NH_2$—CO—, mono- or di$(C_1–C_6)$alkylcarbamoyl, hydroxy $(C_1–C_6)$alkyl, $(C_1–C_6)$cycloalkyl or benzyl, wherein the said benzyl is optionally substituted with one to three substituent(s) each independently being OH, halogen, $NO_2$, $NH_2$, $(C_1–C_6)$alkyl, $(C_1–C_6)$alkoxy, mono- or di$(C_1–C_6)$alkylamino or halo-$(C_1–C_6)$alkyl;

or $R_4$ and $R_5$ form, together with the N-atom to which they are attached, wherein n=1 or 2; $R_6$ is as defined above; and r=0 to 3;

or $R_4$ and $R_5$ form, together with the N-atom to which they are attached, 1-imidazolyl, 1-imidazolinyl or 1-triazolyl, each of which can optionally be substituted with one to three substituent(s) $R_7$ each independently being $(C_1–C_6)$alkyl or $NH_2$;

Ra is H, OH, halogen, $(C_1–C_6)$alkyl, $(C_2–C_6)$alkenyl, $(C_2–C_6)$alkynyl, $(C_1–C_6)$alkoxy, halo$(C_1–C_6)$alkyl, $NO_2$, $NH_2$, mono- or di$(C_1–C_6)$alkylamino or $(C_1–C_6)$alkyl-S—;

Rb is H, OH, halogen, $(C_1–C_6)$alkyl, $(C_2–C_6)$alkenyl, $(C_1–C_6)$alkynyl, $(C_1–C_6)$alkoxy, halo$(C_1–C_6)$alkyl, $NO_2$, $NH_2$, mono- or di$(C_1–C_6)$alkylamino, $(C_1–C_6)$alkyl-S— or CN;

m is 0 to 3; and t is 0 to 3, with the provisos, that when A is a benzene ring, then Ra and Rb are not at the same time H; and the compound is not 4-[4-[(7-Chloro-2-methyl-4-quinolinyl)amino]phenyl]-1-diethylcarbamoylpiperazine.

2. A compound according to claim 1, which is a compound of formula IIB,

IIB or a pharmaceutically acceptable salt or ester thereof, wherein A, $R_1$, $R_2$, $R_3$, $R_4$, $R_5$, m and t are as defined in claim 1; and Ra is H, OH, halogen, $(C_1-C_6)$alkyl, $(C_2-C_6)$alkenyl, $(C_2-C_6)$alkynyl, $(C_1-C_6)$alkoxy, halo$(C_1-C_6)$alkyl, $NO_2$, $NH_2$, mono- or di$(C_1-C_6)$alkylamino or $(C_1-C_6)$alkyl-S—; and Rb is H, OH, halogen, $(C_1-C_6)$alkyl, $(C_2-C_6)$alkenyl, $(C_2-C_6)$alkynyl, $(C_1-C_6)$alkoxy, halo$(C_1-C_6)$alkyl, $NO_2$, $NH_2$, mono- or di$(C_1-C_6)$alkylamino, $(C_1-C_6)$alkyl-S— or ON.

3. A compound according to claim 2, wherein A is a benzene ring.

4. A compound according to claim 3, wherein m is 0 or 1.

5. A compound according to claim 3, wherein $R_3$ is $(C_1-C_6)$alkyl or $(C_1-C_6)$alkoxy.

6. A compound according to claim 3, wherein Ra and Rb are independently H or $(C_1-C_3)$ alkyl, wherein the $(C_1-C_3)$ alkyl includes both straight and branched chain radicals of up to carbon atoms.

7. A compound according to claim 2, wherein the compound is (3-Ethyl-2,8-dimethylquinolin-4-yl)-[4-(4-methylpiperizin-1-yl)phenyl]amine, (2-Methylquinolin-4-yl)-[4-(4-methylpiperazin-1-yl)phenyl]amine, (3-Ethyl-2,6-dimethylquinolin-4-yl)-[4-(4-methylpiperazin-1-yl)phenyl]amine, (3-Ethyl-6-methoxy-2-methylquinolin-4-yl)-[4-(4-methylpiperazin-1-yl)phenyl]amine, (3-Ethyl-2-methylquinolin-4-yl)-[4-(4-methylpiperazin-1-yl)phenyl]amine, 3-Isopropyl-2-methylquinolin-4-yl)-[4-(4-methylpiperazin-1-yl)phenyl]amine, (2,3-Dimethylquinolin-4-yl)-[4-(4-methylpiperazin-1-yl)phenyl]amine or (3-Ethyl-2-methylquinolin-4-yl)-methyl-[4-(4-methylpiperazin-1-yl)phenyl]amine.

8. A compound according to claim 1, wherein $R_4$ and $R_5$ form, together with the N-atom to which they are attached, wherein $R_6$ is $(C_1-C_6)$alkyl, $(C_1-C_6)$alkenyl, $(C_3-C_6)$cycloalkyl or hydroxy$(C_1-C_6)$alkyl.

9. A compound according to claim 8, wherein $R_6$ is $(C_1-C_6)$alkyl.

10. A pharmaceutical composition comprising at least one compound according to claim 1 and a pharmaceutically acceptable diluent, carrier and/or excipient.

11. A method for the antagonism of alpha-2 adrenoceptors, which comprises administering to a mammal in need thereof an effective amount of at least one compound according to claim 1.

12. A method for the treatment of a disorder of the central nervous system, male sexual impotence, orthostatic hypotension, non-insulin dependent diabetes, or obesity, which comprises administering to a mammal in need of the treatment an effective amount of at least one compound according to claim 1.

13. A method for reversing alpha-2 agonistic effects, which comprises administering to a mammal in need thereof an effective amount of at least one compound according to claim 1.

14. The method according to claim 12, which comprises treating a disorder of the central nervous system.

15. The method according to claim 14, wherein the disorder of the central nervous system is depression, anxiety, post-traumatic stress disorder, schizophrenia, Parkinson's disease, or another movement disorder.

* * * * *

UNITED STATES PATENT AND TRADEMARK OFFICE
CERTIFICATE OF CORRECTION

PATENT NO. : 6,593,324 B2
DATED : July 15, 2003
INVENTOR(S) : Wurster et al.

It is certified that error appears in the above-identified patent and that said Letters Patent is hereby corrected as shown below:

Title page,
Item [54], title, "DERVATIVES" should read -- DERIVATIVES --.

Column 26,
Line 11, "$(C_1-C_6)$cycloalkyl" should read -- $(C_3-C_6)$cycloalkyl --.
Line 36, "$(C_1-C_6)$alkynyl," should read -- $(C_2-C_6)$alkynyl, --.

Column 27,
Line 9, "ON." should read -- CN. --.
Lines 12, 13 and 15, "claim 3," should read -- claim 2, --.
Line 18, "to carbon" should read -- to 3 carbon --.

Signed and Sealed this

Twenty-first Day of October, 2003

JAMES E. ROGAN
*Director of the United States Patent and Trademark Office*